(12) United States Patent
Shibaguchi et al.

(10) Patent No.: US 10,324,079 B2
(45) Date of Patent: Jun. 18, 2019

(54) METHOD FOR RAPID TESTING ALLERGY

(71) Applicant: Hirotomo Shibaguchi, Fukuoka-shi, Fukuoka (JP)

(72) Inventors: Hirotomo Shibaguchi, Fukuoka (JP); Yuki Yasutaka, Fukuoka (JP); Kojiro Futagami, Fukuoka (JP)

(73) Assignee: Hirotomo Shibaguchi, Fukuoka-Shi, Fukuoka (JP)

( * ) Notice: Subject to any disclaimer, the term of this patent is extended or adjusted under 35 U.S.C. 154(b) by 37 days.

(21) Appl. No.: 14/767,355

(22) PCT Filed: Feb. 13, 2014

(86) PCT No.: PCT/JP2014/053259
§ 371 (c)(1),
(2) Date: Nov. 12, 2015

(87) PCT Pub. No.: WO2014/126125
PCT Pub. Date: Aug. 21, 2014

(65) Prior Publication Data
US 2016/0069858 A1 Mar. 10, 2016

(30) Foreign Application Priority Data
Feb. 13, 2013 (JP) .................. 2013-025991

(51) Int. Cl.
*G01N 33/50* (2006.01)
*G01N 33/483* (2006.01)

(52) U.S. Cl.
CPC ..... *G01N 33/4833* (2013.01); *G01N 33/5029* (2013.01); *G01N 33/5091* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 2007/0254886 A1 | 11/2007 | Habashita et al. | |
| 2008/0293708 A1 | 11/2008 | Kawahara et al. | |
| 2011/0243993 A1 | 10/2011 | Broo et al. | |
| 2012/0028288 A1 | 2/2012 | Nitta | |

FOREIGN PATENT DOCUMENTS

| | | |
|---|---|---|
| JP | 2008-510765 A | 4/2008 |
| WO | 2005/023771 A1 | 3/2005 |
| WO | 2007/066684 A1 | 6/2007 |
| WO | 2009102453 | 8/2009 |
| WO | 2012/074106 A1 | 6/2012 |

OTHER PUBLICATIONS

Hallab et al. "Hypersensitivity to metallic biomaterials: a review of leukocyte migration inhibition assays." Biomaterials 21(13): 1301-1314, 2000.*
Chen et al. "RACK1 regulates directional cell migration by acting on Gβγ at the interface with its effectors PLCβ and PI3Kγ." Molecular Biology of the Cell 19(9): 3909-3922, 2008.*
Johansson et al. "Revised nomenclature for allergy for global use: Report of the Nomenclature Review Committee of the World Allergy Organization, Oct. 2003." Journal of Allergy and Clinical Immunology 113(5): 832-836, 2004.*
Takada et al. "Clinical Application of Leukocyte Migration Inhibition Test (LMIT) for the Diagnosis of Metal Allergy", Shigaku, vol. 88, No. 1, pp. 9-19, 2000, and English abstract.
Abe et al. "A study of Clinical Significance of Leucocyte Migration Test in Drug Eruption", Japanese Journal of Allergology, vol. 41, No. 12, pp. 1264-1272, Dec. 30, 1998, and English abstract.
Herbrig et al. "Endothelial dysfunction in patients with rheumatoid arthritis is associated with a reduced number and impaired function of endothelial progenitor cells" Ann Rheum Dis, vol. 65, No. 2, pp. 157-163, 2006.
Picardo et al. "Migration stimulating activity in serum of breast cancer patients", The Lancet, vol. 337, Issue 8734, pp. 130-133, Jan. 19, 1991.
Muto et al. "Evaluation of Diagnostic Significance of the Drug-induced Lymphocyte Stimulation Test in Drug Eruptions", The Japanese Journal of Dermatology, vol. 110, No. 10, pp. 1543-1548 (2000) and English abstract.
Suzuki et al. "Drug Lymphocyte Stimulation Test in the Diagnosis of Adverse Reactions to Antiuberculosis Drugs", Chest, vol. 134, No. 5, pp. 1027-1032 (2008).
Somkrua et al. "Association of HLA-B*5801 allele and allopurinol-induced stevens johnson syndrome and toxic epidermal necrolysis: a systematic review and meta-analysis", BMC Medical Genetics, vol. 12, No. 118 (2011).
Yip et al. "HLA Genotype and Carbamazepine-Induced Cutaneous Adverse Drug Reactions: A Systematic Review", Clinical Pharmacology & Therapeutics, vol. 92, No. 6, pp. 757-765 (2012).
Nitta et al. "Quantitative analysis of eosinophil chemotaxis tracked using a novel optical device—TAXIScan", Journal of Immunological Methods, vol. 320, pp. 155-163 (2007).
International Search Report, PCT/JP2014/053529, dated May 20, 2014 (2 pages).

(Continued)

*Primary Examiner* — Emily A Cordas
(74) *Attorney, Agent, or Firm* — Hamre, Schumann, Mueller & Larson, P.C.

(57) ABSTRACT

The present invention provides a method for testing an allergy capable of rapidly and highly accurately testing an allergic reaction. The method can determine whether or not a patient has an allergy or whether or not an agent that may be allergenic to a patient has an allergenicity (an allergic reactivity) in the patient. The method may comprise the steps of causing migration of leukocytes separated from a healthy human or cells of an established cell line with a chemotactic factor contained in a sample such as body fluid or blood of the patient to be tested or a sample stimulated with the agent that may be allergenic to the patient and analyzing the cell kinetics such as migration velocity, migration distance, and migration direction.

9 Claims, 20 Drawing Sheets

(56) References Cited

OTHER PUBLICATIONS

International Preliminary Report on Patentability and Written Opinion; PCT/JP2014/053529, dated Aug. 13, 2015 (7 pages).
Extended European Search Report of European Application No. 14751837.7, dated Dec. 5, 2016, total 15 pages.
Vanto et al., Leukocyte migration inhibition test in children with cow milk allergy, Allergy, vol. 42, No. 8, Nov. 1987, p. 612-618, total 8 pages.
Balli F et al. "Leukocyte migration inhibition factor test as a diagnostic tool for cow's milk allergy", Nutrition Research, vol. 3, No. 2, Mar. 1, 1983, pp. 189-194, ISSN: 0271-5317, total 6 pages.
Matusiewicz R. et al. "In-vitro migration of healthy donor leukocytes in atopic patient sera and of atopic patient leukocytes in sera of healthy donors", Immunologica Polska, vol. 10, Jan. 1, 1985, pp. 131-134, total 4 pages.
Fassas A et al. "Serum migration-inhibitory activity in patients with acute leukemia and early leukemic lymphosarcoma", Clinical Immunology and Immunopathology San Diego, CA, US, vol. 14, No. 3, Nov. 1, 1979, pp. 368-378, ISSN: 0090-1229, totoal 11 pages.
Bertotto A et al. "Serum migration-inhibitory activity in children with acute infectious mononucleosis", Clinical Immunology and Immunopathology, San Diego, CA, US, vol. 19, No. 3, Jun. 1, 1981, pp. 314-318, ISSN: 0090-1229, total 5 pages.
Ambrogi F et al. "Leukocyte migration inhibitory activity in the serum of patients affected by Hodgkin's disease and other immunoproliferative diseases", European Journal of Cancer (1965), Pergamon, vol. 14, No. 10, Oct. 1, 1978, pp. 1107-1112, ISSN: 0014-2964, total 6 pages.
The partial supplementary European Search Report of European application No. 14751837.7, dated Sep. 12, 2016, total 9 pages.

* cited by examiner

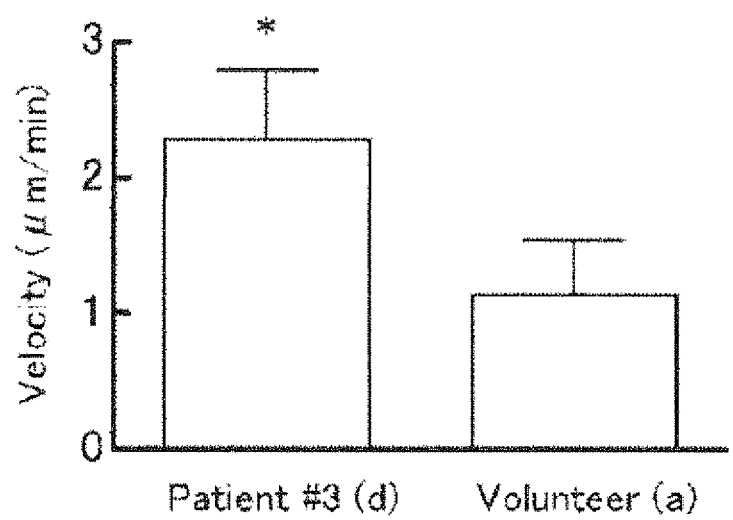

METHOD FOR RAPID TESTING ALLERGY

TECHNICAL FIELD

This application claims the benefit of priority of the prior Japanese patent application (Japanese Patent Application No. 2013-025991) filed on Feb. 13, 2013, the entire contents of which are incorporated herein by reference.

The present invention relates to a method for diagnosing an allergic disease, a method for detecting an agent that is allergenic to or inhibits development of an allergy in a subject, a method for treating or preventing an allergic disease by means of these methods, and a kit to be used in these methods.

BACKGROUND ART

An allergy refers to a phenomenon that an organism develops an excessive immune response to a specific allergenic agent, namely, an antigen designated as an allergen. A variety of foreign substances derived from the environment to which an organism is exposed under its living environment can become an allergen (an allergenic agent) that causes an allergy. Typical allergic diseases induced by various foreign substances, such as pollen, foods, body compositions or dejections of animals, molds, chemicals and drugs, include allergic rhinitis (pollen allergies), allergic conjunctivitis, food allergies, and drug allergies.

These allergic diseases develop when any of the aforementioned allergenic agents, which works as an allergen by itself or does not work as an antigen by itself but is changed to an allergen by binding to a macromolecule such as a protein in the body, elicits an excessive immune response causing an allergy.

Conditions caused by allergies, particularly by drug allergies, include relatively mild drug rashes and blood disorders, severe drug rashes known as Stevens-Johnson syndrome (SJS), toxic epidermal necrolysis (TEN) and drug-induced hypersensitivity syndrome (DINS), as well as serious conditions causing sequela or death at the worst, such as organ dysfunction of, for example, liver, lung or digestive tube, and anaphylactic shock.

Drug withdrawal due to the development of a drug allergy, which means interruption of the treatment of the primary disease, should be avoided by preventing the allergy.

However, means for preventing allergic diseases are limited. Response to a drug is greatly different among individuals and may be influenced by multiple factors including concomitant drugs. Among currently performed allergy tests, an intradermal test or patch test performed in advance to administering a drug cannot always accurately predict development of an allergy to the drug. A drug challenge test is undesirable because it imposes a large burden on the patient and increases risk of shock if an allergy is induced.

Accordingly, once a drug allergy develops, careful and rapid detection and determination of the causative agent is desired.

The causative agent for a drug allergy is currently detected or determined by, for example, a drug-induced lymphocyte stimulation test (DLST) or a leukocyte migration test (LMT). In addition, a time-consuming drug elimination method in which a suspected drug is withdrawn may be employed.

The DLST and the LMT are useful, in view of safety, because blood collected from the patient is tested. The patient is not involved after the blood collection. Disadvantages of the tests include that the tests need approximately 10 ml of blood for each drug to be tested, require about one week for obtaining the result and could give false positive reactions.

A drug allergy can be caused by any of allergic mechanisms including types I to IV. For planning treatment and relief of a symptom presented by a patient, it is important to establish a definitive diagnosis that the symptom is a drug allergy through an immune response or the symptom is a non-allergic adverse reaction (pseudo reaction) involving no immune response.

In a blood test for diagnosing an allergy, indicators such as eosinophils and IgEs are generally measured. Though many of such indicators can be used or referred to for diagnosing an allergic state for example in type I allergy, they are not universal indicators and cannot be used for the definite diagnosis of all types of allergies.

In addition, positive rates are not very high in tests such as the DLST (Non Patent Literatures 1 and 2). One of the reasons is probably that it fails to exclude pseudo reactions different from drug allergies.

On the other hand, it has been revealed that a specific human histocompatibility antigen (HLA) genotype is a risk factor of severe SJS or TEN developed after taking allopurinol, a gout suppressant, or carbamazepine, an antiepileptic drug in south Asians, particularly Chinese people (Non Patent Literatures 3 and 4). Methods for predicting a risk of a drug based on the HLA gene has been developed (Non Patent Literature 5). However, this method is used only for avoiding the risk and is not sufficient.

Accordingly, there is a demand for a method which can test a drug allergy accurately, and a method which can efficiently and sensitively test or determine a drug that could induce a drug allergy, for the purpose of selecting an alternative drug for treating the primary disease in a patient.

CITATION LIST

Non Patent Literature

Non Patent Literature 1: Mika Muto et al., the Japanese Journal of Dermatology, 2000; 110(10): 1543-1548
Non Patent Literature 2: Suzuki Y, et al., CHEST 2008; 134(5): 1027-1032
Non Patent Literature 3: Somkrua R, et al., BMC Med Genet, 2011; 12: 118
Non Patent Literature 4: Yip V L, et al., Clin Pharmacol Ther. 2012; 92(6): 757-65
Non Patent Literature 5: MediBiC Group, Aug. 27, 2012, press release

SUMMARY OF INVENTION

As a result of earnest studies, the present inventors have found that whether or not a subject has an allergy can be rapidly, accurately and efficiently tested by using serum of the subject having an allergy-like symptom and cells such as leukocytes of a healthy volunteer. The present inventors also have found that whether or not an allergenic agent develops an allergy in a subject can be tested by using a reaction solution or culture supernatant obtained by stimulating lymphocytes of the subject with the allergenic agent, and cells such as leukocytes of a healthy volunteer. On the basis of these findings, the inventors have accomplished a very useful and simple method for testing an allergy in a subject, which can be used for identifying an agent that is allergenic to the subject or a method for predicting the risk that the subject develops an allergy.

In one aspect, the present invention provides a method for diagnosing an allergic disease in a subject or determining a risk that a subject develops an allergy, comprising the steps of:

(1) causing migration of chemotactic cells with a sample derived from the subject; and (2) measuring the cell kinetics (for example, the migration distance and/or migration velocity) of the migrating cells.

In another aspect, the present invention provides a method for determining, detecting or quantifying an agent that is allergenic to or inhibits development of an allergy in an animal subject, comprising the steps of:

(1) culturing leukocyte cells derived from the subject in a medium containing a sample;

(2) collecting the culture supernatant;

(3) causing migration of chemotactic cells with the culture supernatant; and (4) measuring the cell kinetics (for example, the migration distance and/or migration velocity) of the migrating cells, wherein the method is for determining whether or not the sample is allergenic to or inhibits development of an allergy in the subject, for detecting an agent that is allergenic to or inhibits development of an allergy in the subject in the sample, or for quantifying an agent that is allergenic to or inhibits development of an allergy in the subject in the sample.

BRIEF DESCRIPTION OF DRAWINGS

FIG. 1a).

FIG. 1a).

FIG. 4E shows analytical results of the migration velocity.

DESCRIPTION OF EMBODIMENTS

Figure 1:
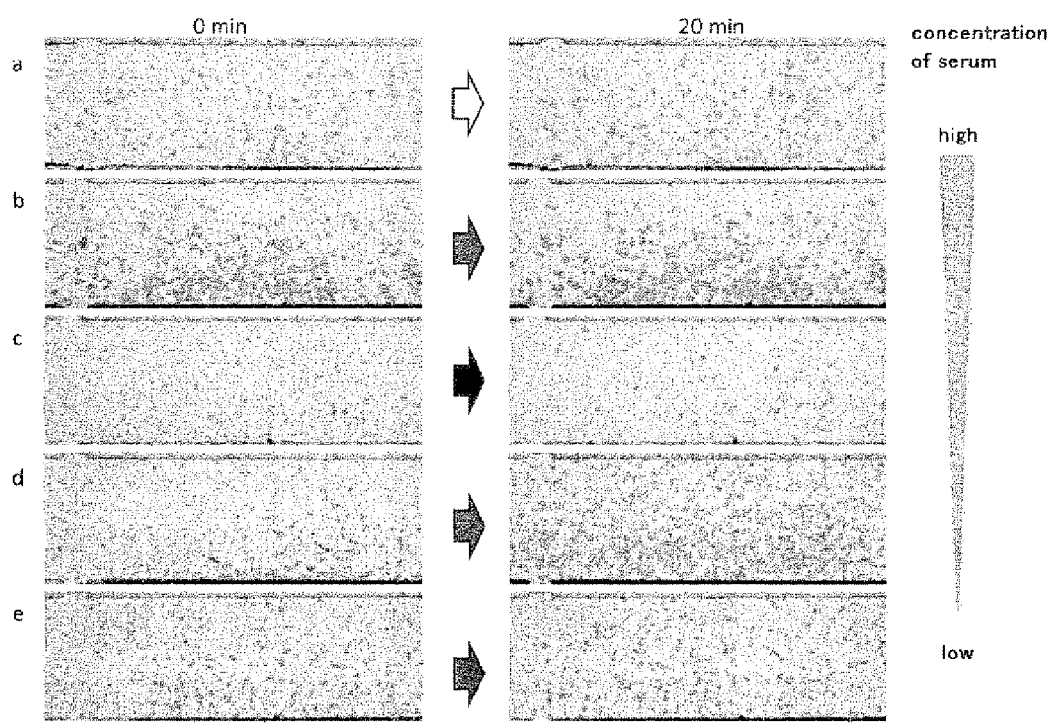
FIG. 1 shows microscopic images of the chemotactic test. Chemotactic cells, i.e. leukocytes were added to the lower well of a chemotactic chamber. Serum derived from a healthy volunteer, a volunteer with mild cutaneous pruritus or a patient suspected of having a drug allergy was added to the upper well of the chamber. The migration of the cells at the addition of the serum and 20 minutes after the addition are shown. Cell kinetics was observed every 2 minutes starting from the addition of the serum and recorded for 20 minutes.

An allergic disease herein may be caused by, and an allergy herein may be, a type I, II, III or IV allergy, such as hives, a food allergy, a pollen allergy, atopic dermatitis, an allergy caused by a chemical, or an allergy caused by a drug. Examples of conditions caused by a drug allergy include drug rashes such as Stevens-Johnson syndrome (SJS), toxic epidermal necrolysis (TEN) and drug-induced hypersensitivity syndrome (DINS). Examples of the drugs that induce an allergy include antibiotics such as penicillins, cephems, aminoglycosides, macrolides, and quinolones, nonsteroidal anti-inflammatory drugs, pyrine drugs (antipyretic analgesics), local anesthetics, iodine-based drugs, central nervous system drugs such as carbamazepine, and gout suppressants such as allopurinol.

The sample used in an aspect of the present invention may be a biological component derived from an animal subject, such as body fluid or blood, and more specifically, its component such as lymph, serum or plasma. The sample used in another aspect of the present invention may be a reactive solution or culture supernatant in which leukocytes from an animal subject were cultured with a candidate agent that may be allergenic to or inhibit development of an allergy in the subject, as well as the candidate agent itself. The amount of the sample used in the aspects of the present invention may be appropriately determined by a person skilled in the art. In one embodiment, the sample may be a very small amount (for example, 1 to 10 µl) of the serum, or a very small amount (for example, 1 ng to 1 µg) of the candidate agent.

The animal subject herein is a mammal, preferably a human.

For example, in the method for diagnosing an allergic disease in a subject or determining a risk that a subject develops an allergy provided by the present invention, the sample may be a biological component of the subject, such as body fluid or blood, more specifically, its component such as lymph or serum. For example, in the method for determining, detecting or quantifying an agent that is allergenic to or inhibits development of an allergy in a subject, the sample may be a reaction solution or culture supernatant obtained by adding an agent that may be allergenic to or may inhibit development of an allergy in the subject to a culture medium comprising leukocytes derived from the subject and stimulating the leukocytes with the agent.

The allergenic agent can be an agent that works as an allergen by itself, or does not work as an antigen by itself but is changed to an allergen by binding to a macromolecule such as a protein in a living body, and may elicit an excessive immune response which causes an allergy in a subject. Typical examples of the allergenic agent include pollen, chemicals, drugs and foods.

The allergy inhibitor is an agent that suppresses development of an allergy in a subject.

The term "chemotaxis" as used herein, which is also mentioned as "migration ability" or "chemical taxis", means a property of an organism including a cell to make a directional migration according to a concentration gradient of a specific chemical substance.

The term "chemotactic factor" as used herein, which is also mentioned as "migration factor", refers to a chemical substance causing the chemotaxis defined above. Typical examples of the chemotactic factor include interleukins, cytokines, and chemokines.

The chemotactic cells herein may be cells having the chemotaxis or migration ability. Examples include leukocytes and established cell lines. The leukocytes may be granulocytes such as neutrophils, eosinophils or basophils, mononuclear cells such as monocytes or lymphocytes, or a mixture thereof.

The chemotactic cells used herein for determining whether or not a subject has an allergy or whether or not an agent develops an allergy in a subject is, for example, leukocytes of a healthy volunteer, particularly leukocytes including granulocytes, which can be simply separated and can respond to all humoral factors (chemotactic factors). Purified and separated neutrophils or eosinophils, or cells of an established cell line expressing a specific receptor may also be used. The use of an established cell line eliminates the step of cell preparation through separation and purification processes and makes the test procedures simple. Examples of the established cell line include human leukocytic cell lines such as human T-cell cell lines (for example, Jurkat cells) and human promyelocytic cell lines (for example, HL-60 cells). Other examples of the human leukocytic cell line include, but are not limited to, HL60RG, K562, MOLT-4F, IM-9, CCRF-HSB2, CCRF-SB, CCRF-CEM, RPMI 8226, RPMI 1788, HLCL-1, HEL, KG-1, BALL-1, TALL-1, P31/FUJ, P30/OHK, P32/ISH, A4/Fuk, A3/KAW, KU812, KU812E, KU812F, KY821, KY821A3, THP-1, LC4-1, SCC-3, KMS-12-BM, KMS-12-PE, PEER, RAJI, U937, CCRF-CEM, MOLT-4, MOLT-3, KG-1, HS-Sultan, WIL2-NS, Saudi, Ramos (RA1), U937 cl1-14, U937 cl1-22, K052, KHM-1B, SKM-1, MLMA, JKT-beta-del, KHYG-1, TK, MY-M12, MY-M13, SLVL, MY, RPMI 8226, RPMI 1788, NC-37, Namalwa, Raji, MEG-01, MEG-O1SSF, MOLT-4, KU812, CCRF-CEM, CMK-86, CMK-11-5, MEG-01s, NOMO-1, NOMO-1s, NKM-1, MEG-A2, NAGL-1, MTA, TMD5, KAI3, Kasumi-4, HL60(S), KHM-10B, K562/ADM, Kasumi-1, Kasumi-3, Kasumi-6, Ki-JK, CPT-K5, NOMO-1/ADM, NCO2, SKNO-1, KMS-11, KMM-1, KMS-2IBM, KMS-26, KMS-27, KMS-28PE, KMS-28BM, KMS-34, KMS-20, TK, KCL-22, PL-21, MKPL-1, NALL-1, RC-K8, HD-70, DL-40, delta-47, PALL-2, FLAM-76, B104, KML-1, STR-428, KMS-33, KHM-2B, Kasumi-2, Kasumi-5, Kasumi-7, Kasumi-8, Kasumi-9, Kasumi-10, Minami-1, Minami-2, KasumiA-541, KasumiA-568, and KasumiA-554.

The cells can be cultured appropriately by a person skilled in the art. For example, the Jurkat cells can be cultured in a DMEM containing 10% FBS and the leukocytes and the mononuclear cells can be cultured in a RPMI 1640 containing 10% FBS.

Migration of the chemotactic cells can be caused by creating a concentration gradient of a chemotactic factor and placing the cells under the concentration gradient. A concentration gradient of a chemotactic factor can be appropriately created by a person skilled in the art. It can be created by using, for example, a chemotaxis chamber such as a Dunn chamber or a µ-Slide. Alternatively, a concentration gradient of a chemotactic factor can be created by creating a concentration gradient of a sample or a culture supernatant containing the chemotactic factor. In one embodiment, on the basis of cell kinetics (for example, migration distance, migration time and/or migration direction) of chemotactic cells in the presence of a concentration gradient of a chemotactic factor contained in a sample, an allergy in a subject is diagnosed, a risk that a subject develops an allergy is determined, and an agent that is allergenic to or inhibits development of an allergy in an animal subject is determined, detected or quantified.

The cell kinetics herein means motility of cells such as chemotaxis or migration ability, and specifically means migration distance, migration time, or migration direction of the cells. The cell kinetics can be measured by observing each cell in a coordinate space in a field of a microscope and sequentially recording the tracks of the migration.

In one embodiment, the methods provided by the present invention can be carried out rapidly, sensitively and/or specifically with a very small amount of a sample. In one embodiment, the amount of blood of a subject necessary for the methods provided by the present invention may be smaller than that necessary for the DLST or the LMT which requires about 10 ml of blood for each test agent. For example, according to this embodiment, the required amount of blood (cells) of a subject may be 100 µl or less for each test agent. In one embodiment, the methods provided by the present invention can provide a result more quickly than the DLST or the LMT which generally takes about 80 hours. For example, according to the present invention, all the steps can be completed in about 2 hours in the diagnosis method using serum or plasma, and in about 30 hours in the other methods.

In one embodiment, the method for diagnosing an allergy in a subject provided by the present invention can determine the severity of the allergic symptom in the subject. For example, as described in Example 1, the method can distinguish a patient having a mild allergic symptom from a patient having a severe allergic symptom. For example, as described in Example 5, when a risk that an allergenic agent causes an allergy in an animal subject (preferably a human) is determined, the possible severity of the allergy to be developed by the agent can be determined.

A person skilled in the art can use an appropriate measuring system for measuring cell kinetics (for example, migration distance and/or migration velocity) of migrating cells. For example, a system that enables a person skilled in the art to sequentially observe and record cell kinetics of each cell in the presence of a concentration gradient of a chemotactic factor contained in a test liquid (serum) in an appropriate coordinate space within a field of a microscope, for example a chemotaxis chamber such as a Dunn chamber or a μ-Slide, may be used. A system which is not integrated with a microscope may also be used as long as cell kinetics of each cell can be sequentially observed and recorded.

In one embodiment, cell kinetics (for example, migration distance and/or migration velocity) of migrating cells can be measured by processing images which are obtained by sequentially observing and recording the cell kinetics of each chemotactic cell with an image processing software, for example those provided free of charge or commercially available, and calculating various parameters concerned with chemotaxis or migration ability of the cells such as time, distance and direction of the migration.

According to the method provided by the present invention, whether or not an animal subject (preferably a human subject) has an allergic disease, whether or not an animal subject has a risk of developing an allergy, whether or not a sample is an agent that is allergenic to an animal subject, whether or not a sample contains an agent that is allergenic to a an animal subject, whether or not a sample is an agent that inhibits an allergy in a subject, or whether or not a sample contains an agent that inhibits an allergy in a subject can be determined on the basis of data of the cell kinetics (for example, migration distance and/or migration velocity) of the migrating cells.

For example, in the method for diagnosing an allergic disease in an animal subject or determining a risk that an animal subject develops an allergy provided by the present invention comprising the steps of:

(1) causing migration of chemotactic cells with a sample derived from the subject; and (2) measuring the cell kinetics (for example, the migration distance and/or migration velocity) of the migrating cells, whether or not the subject has an allergic disease or whether or not the subject has a risk of developing an allergy may be determined by testing a negative control and/or a positive control in addition to the sample derived from the subject. Examples of the negative control include, but are not limited to, samples (for example, serum) derived from a healthy animal (preferably a human) or an animal (preferably a human) not having an allergic disease. Examples of the positive control include a culture supernatant obtained by stimulating leukocyte cells (for example, mononuclear cells) with a leukocyte stimulator. Such a culture supernatant can be prepared, for example, by adding a leukocyte stimulator to a culture medium of leukocyte cells and culturing the cells for a period of time (for example, for one day, two days, three days, four days or five days). Examples of the leukocyte stimulator include a mitogen. Specific examples of the leukocyte stimulators include, but are not limited to, plant lectins such as PHA, concanavalin A and PWM (pokeweed mitogen), LPS (lipopolysaccharide), PPD (purified protein derivative of tuberculin), and dextran sulfate.

For example, when migration distance of migrating cells caused by a sample (for example, serum) derived from an animal subject (preferably a human) are longer than migration distance of migrating cells caused by a sample (for example, serum) derived from a healthy animal (preferably a human) or an animal (preferably a human) not having an allergic disease as a negative control, the animal subject (preferably the human) can be determined to have an allergic disease or a risk of developing an allergy. In one embodiment, when migration distance of migrating cells caused by a sample (for example, serum) derived from an animal subject (preferably a human) are 1.2, 1.3, 1.4, 1.5, 1.6, 1.7, 1.8, 1.9 or 2 times or more longer than that caused by a sample (for example, serum) derived from a healthy animal (preferably a human) or an animal (preferably a human) not having an allergic disease, the animal subject (preferably the human) can be determined to have an allergic disease or a risk of developing an allergy.

Alternatively, when migration velocity of migrating cells caused by a sample (for example, serum) derived from an animal subject (preferably a human) is higher, for example, 1.2, 1.3, 1.4, 1.5, 1.6, 1.7, 1.8, 1.9 or 2 times or more higher than that caused by a sample (for example, serum) derived from a healthy animal (preferably a human) or an animal (preferably a human) not having an allergic disease, the animal subject (preferably the human) can be determined to have an allergic disease or a risk of developing an allergy.

On the other hand, when value of migration distance and/or migration velocity of migrating cells caused by a sample (for example, serum) derived from an animal subject (preferably a human) is 1.1, 1, 0.9 or 0.8 times as or less than that caused by a sample (for example, serum) derived from a healthy animal (preferably a human) or an animal (preferably a human) not having an allergic disease, the subject can be determined not to have an allergic disease or a risk of developing an allergy.

Furthermore, when value of migration distance and/or migration velocity of migrating cells caused by a sample (for example, serum) derived from an animal subject (preferably, a human) is equivalent to or larger, for example, 1, 1.1, 1.2, 1.3, 1.4, 1.5, 1.6, 1.7, 1.8, 1.9 or 2 times or more larger than that caused by a culture supernatant of leukocyte cells stimulated with PHA as a positive control, the animal subject can be determined to have an allergic disease or a risk of developing an allergy.

In the method for diagnosing an allergic disease in a subject or for determining a risk that a subject develops an allergy provided by the present invention, the positive control or the negative control as described above can be used alone or in combination.

In one embodiment, the method for diagnosing an allergic disease in a subject or for determining a risk that a subject develops an allergy provided by the present invention can be employed for determining the degree of the allergic disease or the degree of the risk. For example, the degree of an allergic disease in a subject or the degree of a risk that a subject develops an allergy may be determined by generating a calibration curve on the basis of migration distance and/or migration velocity of a given amount of migrating cells caused with a plurality of known amounts of a positive control (for example, culture supernatants prepared by stimulating leukocyte cells such as mononuclear cells with different concentrations of a leukocyte stimulator such as PHA), and quantifying a test result of a sample derived from an animal subject (preferably, a human) with the calibration curve.

In one embodiment, time-dependent change of the degree of an allergic disease in an animal subject or the degree of a risk that an animal subject develops an allergy may be determined by collecting samples from the animal subject (preferably, a human) at different time points, testing the samples by the method for diagnosing an allergic disease in a subject or for determining a risk that a subject develops an allergy provided by the present invention, and comparing migration distance and/or migration velocity of migrating cells caused by the collected samples at each time. For example, if value of migration distance and/or migration velocity of migrating cells is larger than that caused by the sample previously collected from the same animal subject (preferably, the same human), it can be determined that the allergic symptom has become worse, or that the risk that the subject develops the allergy has been increased. On the other hand, for example, if value of migration distance and/or migration velocity of migrating cells is smaller than that caused by the sample previously collected from the same animal subject (preferably, the same human), it can be determined that the allergic symptom has been ameliorated or that the risk that the subject develops the allergy has been reduced.

In one embodiment, the method for diagnosing an allergic disease provided by the present invention can be utilized for a differential diagnosis of an allergic disease from a non-allergic disease. For example, when serum derived from a subject suspected of having drug rashes and serum derived from a healthy human or from a patient of a non-allergic disease are tested and migration distance and/or migration velocity of migrating cells measured for the serum derived from the subject is longer and/or higher than that measured for the serum derived from the healthy human or the patient of the non-allergic disease, the subject is diagnosed as having an allergic disease.

In one embodiment, whether or not an animal subject has an allergic disease or has a risk of developing an allergy can be determined by measuring migration distance of chemotactic cells during a fixed time period and classifying the result in four classes of: negative (−), no or substantially no chemotactic factor in the sample; suspected (+/−), a chemotactic factor is suspected to be present; positive (+), a chemotactic factor is present; and strongly positive (++), a chemotactic factor is present in a higher concentration.

In the method provided by the present invention for determining or detecting an agent that is allergenic to or inhibits development of an allergy in an animal subject comprising the steps of:

(1) culturing leukocyte cells (for example, mononuclear cells) derived from the animal subject in a medium containing a sample;

(2) collecting the culture supernatant;

(3) causing migration of chemotactic cells with the culture supernatant; and (4) measuring the cell kinetics (for example, the migration distance and/or migration velocity) of the migrating cells, leukocyte cells (for example, mononuclear cells) derived from a healthy animal may be used in place of leukocyte cells (for example, mononuclear cells) derived from the animal subject, for determining whether or not the sample is an agent that is allergenic to or inhibits development of an allergy in the animal subject, or whether or not the sample contains an agent that is allergenic to or inhibits development of an allergy in the animal subject. A positive control may be tested as well as the sample, for determining whether or not the sample is an agent that is allergenic to or inhibits development of an allergy in the animal subject, or whether or not the sample contains an agent that is allergenic to or inhibits development of an allergy in the animal subject. Examples of the positive control include a leukocyte stimulator such as a mitogen. Specific examples of the positive control include, but are not limited to, plant lectins such as PHA, concanavalin A and PWM, LPS, PPD, and dextran sulfate.

For example, when leukocyte cells (for example, mononuclear cells) derived from a healthy animal (preferably, a human) is used in place of leukocyte cells (for example, mononuclear cells) derived from an animal subject (preferably, a human) and value of migration distance and/or migration velocity of migrating cells obtained with the leukocyte cells (for example, the mononuclear cells) derived from the animal subject (preferably, the human) is larger, for example, 1.2, 1.3, 1.4, 1.5, 1.6, 1.7, 1.8, 1.9 or 2 times or more larger than that obtained with the leukocyte cells (for example, the mononuclear cells) derived from the healthy animal (preferably, the human), it can be determined that the sample is or contains an agent that is allergenic to the animal subject.

Furthermore, if the value of migration distance and/or migration velocity of migrating cells caused by PHA as a positive control is equivalent to or larger, for example, 1, 1.1, 1.2, 1.3, 1.4, 1.5, 1.6, 1.7, 1.8, 1.9 or 2 times or more larger than that obtained for the sample, it can be determined that the sample is or contains an agent that is allergenic to the animal subject.

For example, if the value of migration distance and/or migration velocity of migrating cells obtained for a mixture containing PHA and a sample is smaller, for example, 0.5 times or less smaller than that obtained for PHA, it is determined that the sample is or contains an agent that inhibits development of an allergy in the animal subject.

In the method for determining or detecting an agent that is allergenic to or inhibits development of an allergy in an animal subject provided by the present invention, leukocyte cells (for example, mononuclear cells) derived from a healthy animal (preferably, a human) may be used in place of leukocyte cells (for example, mononuclear cells) derived from the animal subject (preferably, the human subject), and/or a positive control may be further tested in addition to the sample.

In one embodiment, it can be determined that a sample is or contains an agent that is allergenic to or inhibits development of an allergy in the animal subject by measuring migration time necessary for chemotactic cells migrating through a fixed distance and classifying the results in four classes of: negative (−), no or substantially no chemotactic factor in the sample; suspected (+/−), a chemotactic factor is suspected to be present; positive (+), a chemotactic factor is present; and strongly positive (++), a chemotactic factor is present in a higher concentration.

In one embodiment, a chemotactic factor is released from leukocyte cells derived from a subject in proportion to the concentration of an allergenic agent or an allergy inhibitor and chemotactic cells migrates. Accordingly, when determining whether or not an agent that is allergenic to the animal subject is contained in the sample, the sample may be serially diluted and the concentration-dependent change of the cell kinetics (for example, the migration distance and/or migration velocity) of the chemotactic cells may be detected.

In the method provided by the present invention for quantifying an agent that is allergenic to or inhibits development of an allergy in an animal subject in a sample comprising the steps of:

(1) culturing leukocyte cells (for example, mononuclear cells) derived from the animal subject in a medium containing a known amount of the agent that is allergenic to the subject, a known amount of the agent that inhibits development of an allergy in the subject, or the sample;
(2) collecting the culture supernatant;
(3) causing migration of chemotactic cells with the culture supernatant; and
(4) measuring the cell kinetics (for example, the migration distance and/or migration velocity) of the migrating cells, the agent that is allergenic to or inhibits development of an allergy in the subject in the sample can be quantified by comparing the cell kinetics (for example, the migration distance and/or migration velocity) of the migrating cells measured in the presence of the known amount of the agent that is allergenic to the subject or a known amount of the agent that inhibits development of an allergy in the subject with that of the migrating cells measured in the presence of the sample.

In one embodiment, an agent that is allergenic to or inhibits development of an allergy in the subject can be quantified with a calibration curve of the migration distance and/or migration velocity that is generated by testing a plurality of known concentrations of the agent that is allergenic to or inhibits development of an allergy in the subject.

The method for determining a risk that a subject develops an allergy provided by the present invention can be used for predicting whether or not a test agent induces an allergy in the subject. Accordingly, in one embodiment, the method for determining a risk that a subject develops an allergy provided by the present invention is applicable as a novel method for predicting the development of the allergy in the subject and is extremely useful.

If the method for determining a risk that a subject develops an allergy provided by the present invention is utilized as the method for predicting the development of the allergy in the subject, a necessary amount of a sample is smaller than that in the DLST or the LMT, in which about 10 ml of a sample is necessary for each drug to be tested. For example, the required amount of blood (cells) of a subject may be 100 µl or less for each drug to be tested. This property of the method, that is, it does not require blood or cells of a subject as much as that required in the DLST or the LMT, is very advantageous since the burden on the subject is reduced.

In one embodiment, the methods provided by the present invention comprises the steps of:

preparing a sample containing serum of the subject or a sample containing a chemotactic factor generated by exposing leukocytes of the subject to a test agent such as a test chemical, a test drug or a test food that may be allergenic to or may inhibit the development of an allergy in the subject;

preparing chemotactic cells from, for example, blood of the subject or a healthy human;

measuring the cell kinetics of the cells;

processing an image of the cell kinetics; and, determining whether or not the subject has an allergic disease, whether or not the subject has a risk of developing an allergy, whether or not the test agent is an agent that is allergenic to or inhibits development of an allergy in the subject, or whether or not the test agent contains an agent that is allergenic to or inhibits development of an allergy in the subject on the basis of the processed image.

In the step of preparing the sample, the sample suitable to an allergy test is prepared by a conventional method from a biological component such as body fluid or blood of the subject. For example, if serum is used as the sample, the sample can be prepared by adding a serum separating agent to blood collected from the subject and centrifuging the mixture. Other samples can be prepared similarly by a conventional method.

When the methods provided by the present invention is used for determining or testing whether or not an agent is allergenic to or inhibits development of an allergy in the subject, or for predicting whether or not an agent induces an allergy in the subject, the sample to be tested may be a solution containing a chemotactic factor that is secreted from leukocytes exposed to the agent to be tested.

In the step of preparing the chemotactic cells, the chemotactic cells can be prepared, for example, by adding an agent such as heparin or EDTA to blood from a healthy volunteer having no allergic symptom, separating leukocytes including granulocytes such as neutrophils with density gradient centrifugation in a conventional manner, and suspending the separated leukocytes in an appropriate culture medium. Alternatively, cells of an established cell line expressing a specific receptor can be used as the chemotactic cells. Such chemotactic cells can be prepared by suspending the cells of the cell line in an appropriate culture medium.

In the step of measuring the cell kinetics, for example, a fixed amount of the chemotactic cells is injected into the lower well of a commercially available holder for testing chemotactic cells and sucked up to the end of an observation terrace, and a fixed amount of the sample such as serum is injected into the upper well to generate a concentration gradient of the sample, and an image of the chemotactic cells formed on the observation terrace is measured.

In the step of processing the image, the image of the chemotactic cells formed in the step of measuring the cell kinetics is analyzed with an image processing software and various parameters such as migration distance, migration time and migration direction of the chemotactic cells in the presence of the sample such as serum are calculated.

In the step of the determination, the presence or absence of an allergic reaction in the subject and the degree thereof, which is caused by an agent that is allergenic to or inhibits development of an allergy in the subject in a sample such as serum, can be determined by comparing various parameters obtained in the step of processing an image with predetermined criteria. Similarly, whether or not the subject has an allergic disease or whether or not the subject has a risk of developing an allergy can be determined, or an agent that is allergenic to or inhibits development of an allergy in the subject is determined, detected or quantified.

In one embodiment, the methods provided by the present invention are carried out in vitro. A result obtained by the method for determining a risk that a subject develops an allergy or the method for determining, detecting or quantifying an agent that is allergenic to or inhibits development of an allergy in a subject provided by the present invention can assist a doctor to diagnose an allergic disease.

An allergy can be treated or prevented according to a result of the method for diagnosing an allergy in a subject, the method for determining a risk that a subject develops an allergy, or the method for determining, detecting or quantifying an agent that is allergenic to a subject provided by the present invention. For example, if an agent that is allergenic to a subject is determined by the method for determining, detecting or quantifying an agent that is allergenic to an animal subject provided by the present invention, the allergy can be treated or prevented by reducing the contact of the subject with the agent. Alternatively, for example, if a subject is determined to have an allergic disease or not to have an allergic disease but have a high risk of developing an allergic disease by the method for diagnosing an allergy in a subject or the method for determining a risk that a subject develops an allergy provided by the present invention, the allergy can be treated or prevented by administering an anti-allergic agent (for example, an antihistamine). Accordingly, in one embodiment, the present invention provides a method for treating or preventing an allergy in a subject comprising carrying out the method for diagnosing an allergy in a subject, the method for determining a risk that a subject develops an allergy, or the method for determining, detecting or quantifying an agent that is allergenic to a subject provided by the present invention. In one embodiment, the method for treating or preventing an allergy may further comprise the step of reducing a contact of the subject with the agent that is allergenic to the subject and/or the step of administering an anti-allergic agent to the subject. For example, if the symptom of the allergy is drug rashes, the method may comprise the step of stopping administration of the causative drug.

In one embodiment, the present invention provides a kit comprising a chemotaxis chamber, leukocytes or an established cell line, and a cell culture medium for diagnosing an allergic disease in a subject; for determining a risk that a subject develops an allergy; or for determining, detecting or quantifying an agent that is allergenic to or inhibits development of an allergy in a subject. The leukocytes can be prepared from, for example, blood of a healthy human. Examples of the established cell line include human leukocytic cell lines such as human T-cell cell lines (for example, Jurkat cells) and human promyelocytic cell lines (for example, HL-60 cells). Other examples of the human leukocytic cell line include, but are not limited to, HL60RG, K562, MOLT-4F, IM-9, CCRF-HSB2, CCRF-SB, CCRF-CEM, RPMI 8226, RPMI 1788, HLCL-1, HEL, KG-1, BALL-1, TALL-1, P31/FUJ, P30/OHK, P32/ISH, A4/Fuk, A3/KAW, KU812, KU812E, KU812F, KY821, KY821A3, THP-1, LC4-1, SCC-3, KMS-12-BM, KMS-12-PE, PEER, RAJI, U937, CCRF-CEM, MOLT-4, MOLT-3, KG-1, HS-Sultan, WIL2-NS, Daudi, Ramos (RA1), U937 cl1-14, U937 cl1-22, K052, KHM-1B, SKM-1, MLMA, JKT-beta-del, KHYG-1, TK, MY-M12, MY-M13, SLVL, MY, RPMI 8226, RPMI 1788, NC-37, Namalwa, Raji, MEG-01, MEG-01SSF, MOLT-4, KU812, CCRF-CEM, CMK-86, CMK-11-5, MEG-01s, NOMO-1, NOMO-1s, NKM-1, MEG-A2, NAGL-1, MTA, TMD5, KAI3, Kasumi-4, HL60(S), KHM-10B, K562/ADM, Kasumi-1, Kasumi-3, Kasumi-6, Ki-JK, CPT-K5, NOMO-1/ADM, NCO2, SKNO-1, KMS-11, KMM-1, KMS-21BM, KMS-26, KMS-27, KMS-28PE, KMS-28BM, KMS-34, KMS-20, TK, KCL-22, PL-21, MKPL-1, NALL-1, RC-K8, HD-70, DL-40, delta-47, PALL-2, FLAM-76, B104, KML-1, STR-428, KMS-33, KHM-2B, Kasumi-2, Kasumi-5, Kasumi-7, Kasumi-8, Kasumi-9, Kasumi-10, Minami-1, Minami-2, KasumiA-541, KasumiA-568, and KasumiA-554. The leukocytes or the established cell line can be provided in a cryopreserved state. Examples of the cell culture medium include DMEM and RPMI 1640. The kit may further comprise PHA that can be used as a positive control. The kit may further comprise an agent for staining cells, preferably a reagent capable of staining living cells (for example, POLARIC-500c6F), so that the cells can be easily observed under a microscope. In one embodiment, the present invention provides a device comprising a recorder for sequentially recording microscopic images of migration of cells and an image analyzer for analyzing the microscopic images to calculate migration distance and migration velocity of the cells, for diagnosing an allergic disease in a subject; for determining a risk that a subject develops an allergy; or for determining, detecting or quantifying an agent that is allergenic to a subject. The device may additionally comprise the aforementioned kit. The kit and the device can be used in the methods provided by the present invention.

The present invention further provides the following embodiments:

(a) A method for testing an allergy in an animal subject comprising, creating a test concentration gradient of body fluid collected from the animal subject, and observing the cell kinetics of chemotactic cells depending on the presence or absence of a chemotactic factor contained in the body fluid or the concentration thereof in the test concentration gradient.

(b) The method for testing an allergy in an animal subject according to (a), characterized in that a control concentration gradient is created with control body fluid collected from a control animal having no allergic symptom, the cell kinetics of the chemotactic cells depending on the presence or absence of a chemotactic factor contained in the control body fluid or the concentration thereof is observed in the control concentration gradient, and the motility of the chemotactic cells in the test concentration gradient is compared with the motility of the chemotactic cells in the control concentration gradient.

(c) A method for determining or testing an agent that is allergenic to an animal subject, which is for determining a causative agent for an allergy developed in an animal subject, in which a suspected agent that is suspected to cause the allergy in the animal subject is mixed with body fluid that contains at least lymphocytes and is collected from the animal subject to give a test mixture, a test concentration gradient is created with the test mixture, and the cell kinetics of chemotactic cells depending on the presence or absence of a chemotactic factor contained in the test mixture or the concentration thereof is observed in the test concentration gradient.

(d) The method for determining or testing an agent that is allergenic to an animal subject according to (c), in which body fluid that contains at least lymphocytes and is collected from a control animal that has no allergy at least for the suspected agent is mixed with the suspected agent to give a control mixture, a control concentration gradient is created with the control mixture, and the cell kinetics of chemotactic cells depending on the presence or absence of a chemotactic factor contained in the control mixture or the concentration thereof is observed in the control concentration gradient, and the motility of the chemotactic cells in the test concentration gradient is compared with the motility of the chemotactic cells in the control concentration gradient.

(e) A method for predicting an allergy in a subject, which is for determining or testing a causative agent for an allergy in an animal subject before the animal subject develops an allergy, in which a suspected agent that is suspected to cause an allergy when used for or taken by the animal subject is mixed with body fluid that contains at least lymphocytes and is collected from the animal subject to give a test mixture, a test concentration gradient is created with the test mixture, and the cell kinetics of chemotactic cells depending on the presence or absence of a chemotactic factor contained in the test mixture or the concentration thereof is observed in the test concentration gradient.

(f) The method for predicting an allergy in a subject according to (e), in which body fluid that contains at least lymphocytes and is collected from a control animal that has no allergy at least for the suspected agent is mixed with the suspected agent to prepare a control mixture, a control concentration gradient is created with the control mixture, and the cell kinetics of chemotactic cells depending on the presence or absence of a chemotactic factor contained in the control mixture or the concentration thereof is observed in the control concentration gradient, and the motility of the chemotactic cells in the test concentration gradient is compared with the motility of the chemotactic cells in the control concentration gradient.

In methods (a) to (f) described above, the animal subject and the control animal may include both a human and a non-human animal. The animal subject and the control animal are preferably animals of the same species. Specifically, if the animal subject is a human, the control animal is preferably a human, and if the animal subject is a mouse, the control animal is preferably a mouse.

In method (b) described above, the control animal having no allergic symptom includes an animal having no allergic symptom and an animal having a slight allergy but having no subjective allergic symptom.

The present invention will be described in more detail with reference to examples. The present invention is not limited to the following examples at all. The examples are intended to illustrate the present invention more specifically. Modifications and changes that those skilled in the art can easily contemplate from the following examples shall be embraced within the scope of the present invention.

EXAMPLES

Example 1: Detection of Drug Allergy Patient by Utilizing Migration of Leukocytes Derived from Healthy Human (Patients to be Tested)

Blood withdrawal from patients having a drug allergy-like symptom and healthy volunteers, and collection and use of leukocytes have been applied to and approved by the Institutional Review Board of Fukuoka University Hospital for a clinical study mainly using the LMT. Patients who are candidates for the test were provided with explanation about the clinical study. Informed consent regarding the agreement and cooperation for the clinical study was obtained in written form. Serum and reaction solutions stimulated with antigens prepared for the LMT and remained were used, the LMT being for the patients who had developed a drug allergy-like symptom in the university hospital and needed determination of the agent inducing the allergy-like symptom.

(Patient #1)

Hypersensitivity Reaction: Pancytopenia

Suspected drugs: Nafamostat mesilate (Naotamin), Nifedipine (Sepamit-R, Adalat-CR)

Clinical course: The pancytopenia was not improved after changing and withdrawing the suspected drugs.

Accordingly, the symptom is unlikely to be caused by development of a drug allergy to the suspected drugs.

(Patient #2)

Hypersensitivity reaction: fever of unknown origin (39.0° C.)

Suspected drugs: Levofloxacin hydrate (Cravit), Doripenem hydrate (Finibax)

Clinical course: The patient had a fever of unknown origin before or after administration of the suspected drugs. The fever naturally abated.

Accordingly, the symptom is very unlikely to be caused by development of a drug allergy to the suspected drugs.

(Patient #3)

Hypersensitivity Reaction: Eosinophilia

Suspected drugs: Mosapride citrate hydrate (Gasmotin), Sulpride (Dogmatyl), Rabeprazole sodium (Pariet)

Clinical course: The eosinophils were reduced and the hypersensitivity reaction was improved after withdrawing the suspected drugs.

Accordingly, the symptom was strongly suspected to be caused by a drug allergy, and the causative agent is considered to be at least one of the suspected drugs.

(Serum)

Blood samples from each subject (a healthy volunteer or a volunteer with mild cutaneous pruritus, and the patient suspected of having a drug allergy) were added with a serum separating agent and allowed to stand at room temperature. Serum was separated by centrifugation at 2,000 rpm for 30 minutes or by using Tube 21 (Registered Trademark)—S (Sekisui Chemical Co., Ltd., Osaka).

(Chemotactic Cells)

Leukocytes including granulocytes such as neutrophils were separated from heparinized blood of a healthy volunteer who had no allergic symptom by the density gradient centrifugation (Lymphocyte (Registered Trademark)—poly: CEDARLANE Labs. Ltd., Ontario, Canada) in accordance with a conventional method, and suspended in 5 ml of a culture medium (RPMI 1640: Sigma-Aldrich, MO, USA). After culturing the cells in a $CO_2$ incubator at 37° C. for 1 hour the cells was adjusted to the concentration of about $5 \times 10^5$ cells/ml and used as chemotactic cells.

(Measurement of Cell Kinetics)

The chemotactic cells were injected into the lower well in the holder of EZ-TAXIScan™ (GE Healthcare, Tokyo) at about 5 µl/well, and were drawn to the end of the observation terrace by suction. Subsequently, the serum was injected into the upper well at 1.5 µl/well with a microsyringe to create a concentration gradient on the observation terrace, and images of the chemotactic cells on the observation terrace were sequentially recorded. The depth of the terrace was 4 µm.

(Analysis of Images)

The kinetics of the chemotactic cells migrating on the observation terrace was analyzed with software for processing images, ImageJ (NIH, MD, USA). Various parameters concerned with chemotaxis or migration ability of the cell toward the serum such as velocity, distance and direction of the migration were calculated. The statistical analysis was performed using GraphPad Prism (Registered Trademark) (GraphPad Software, CA, USA).

The cell kinetics after the addition of 1.5 µl of the serum to the upper well was analyzed using images recorded under microscope every two minutes for 20 minutes. Images obtained at the start and end of the observation are shown in FIG. 1. The migration of the chemotactic cells on the observation terrace was successfully observed. FIG. 1 shows the images obtained using the serum of the healthy volunteer (a), the patients #1 to #3 (b to d), and the volunteer with cutaneous pruritus (e).

The polygonal lines on the observation terrace correspond to the tracks of the cells used in the analysis. In (a), (b), and (c), the migration of the cells lacked direction and the migration distance was small. In (d) and (e), the movement of the cells was linear and the migration distance was longer than in (a), (b), and (c). Furthermore, in (d) and (e) the cells successively entered the observation terrace and many cells were on the observation terrace at the end of the analysis.

Figure 2A:
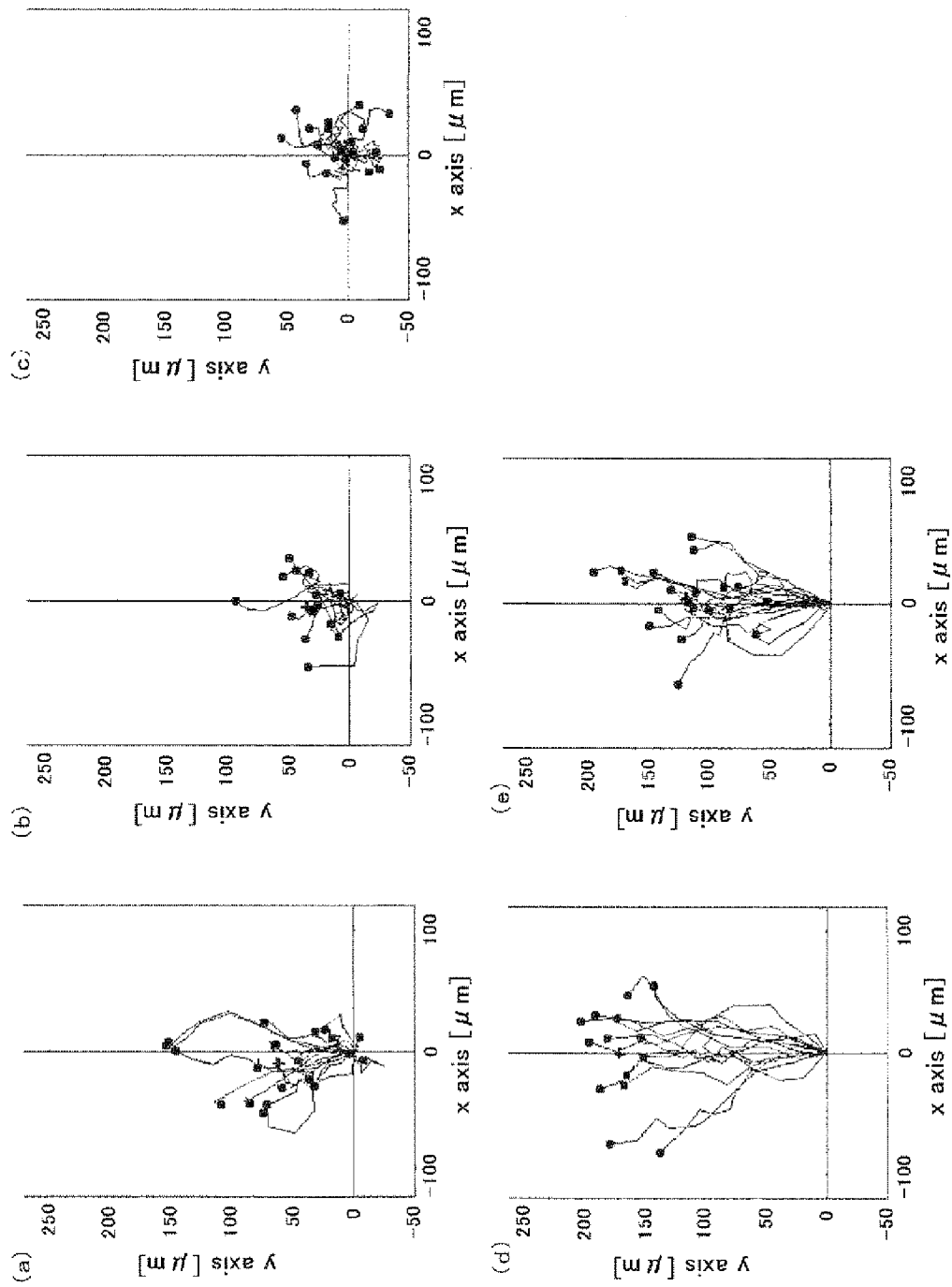
FIG. 2A shows the spatially coordinated migration of the individual cells in reference to the original place where the cells were at the time of starting the observation.
Figure 2B:
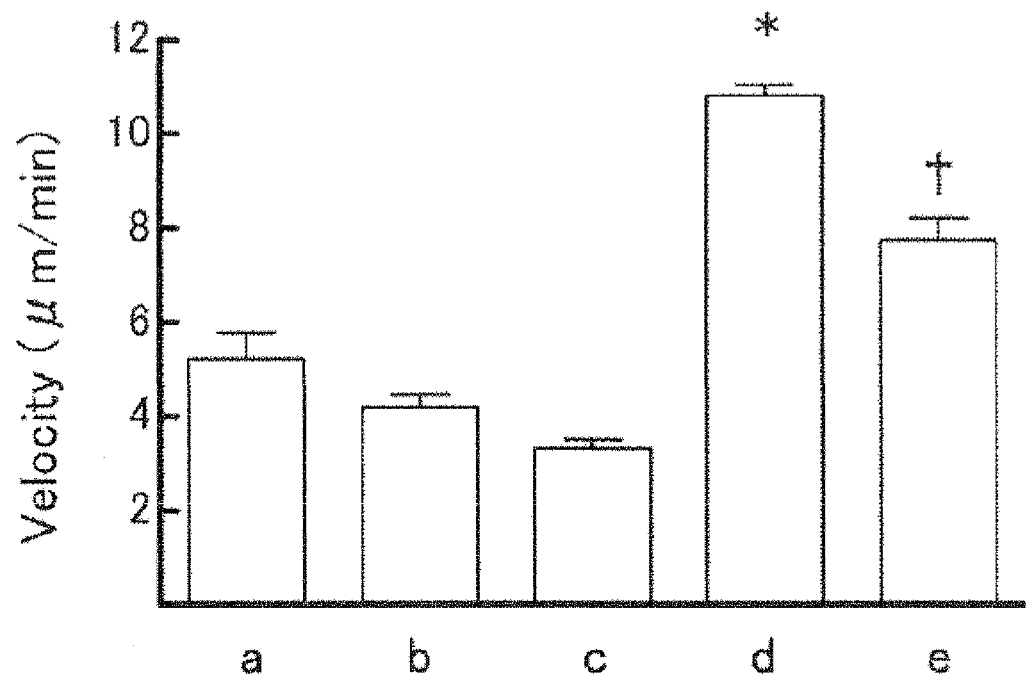
FIG. 2B shows analytical results of the migration velocity.
Figure 2C:
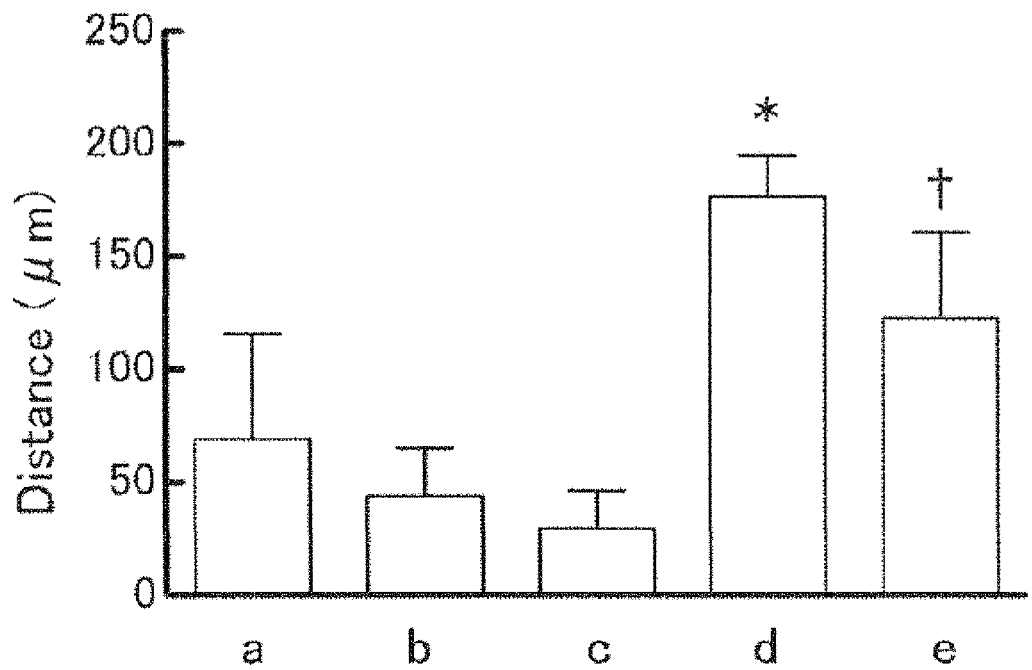
FIG. 2C shows analytical results of the migration distance.

The cell migration of some selected cells was analyzed. FIG. 2 shows the results. FIG. 2A shows the spatially coordinated migration of the individual cells in reference to the original place where the cells were at the time of starting the observation at the origin. FIGS. 2B and 2C show analytical results of the migration velocity and the migration distance, respectively. As expected, little change in both parameters were seen for the healthy volunteer (a) and patients #1 and #2 (b and c) who are unlikely to have a drug allergy according to the clinical courses. On the other hand, for patient #3 (d) who is strongly suspected to have a drug allergy and the volunteer (e) with mild cutaneous pruritus, the parameters were significantly different from those of all the other groups.

(Criteria)

Figure 3A:
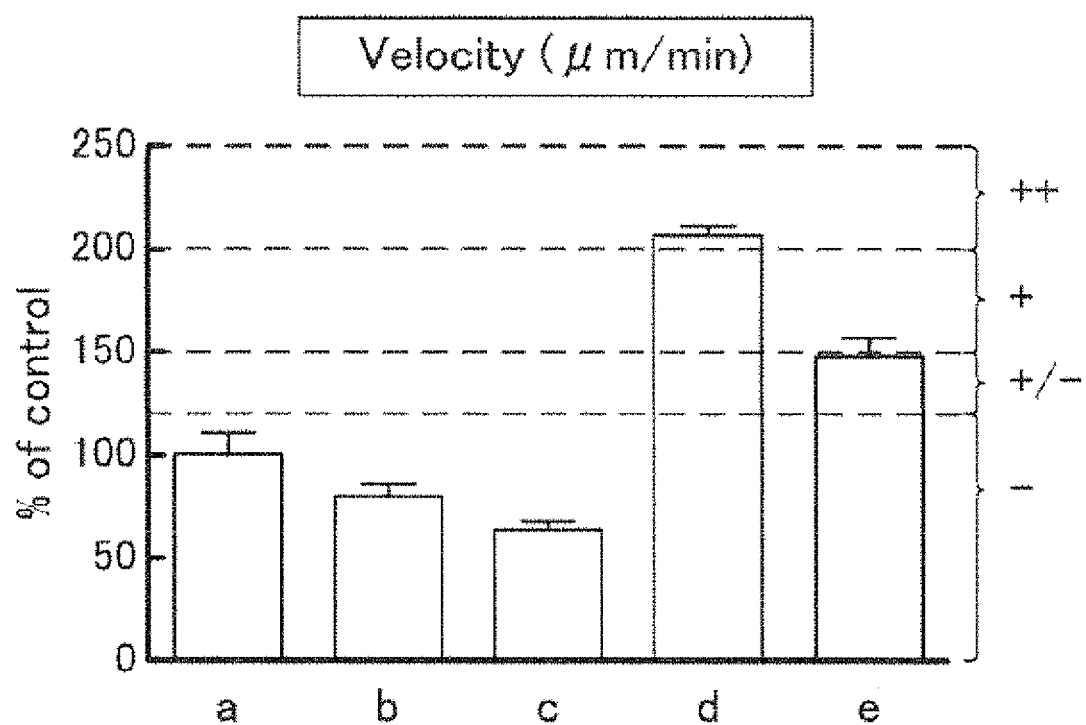
FIG. 3A shows percentages of the migration velocity relative to that of the control group (the serum of the healthy volunteer.
Figure 3B:
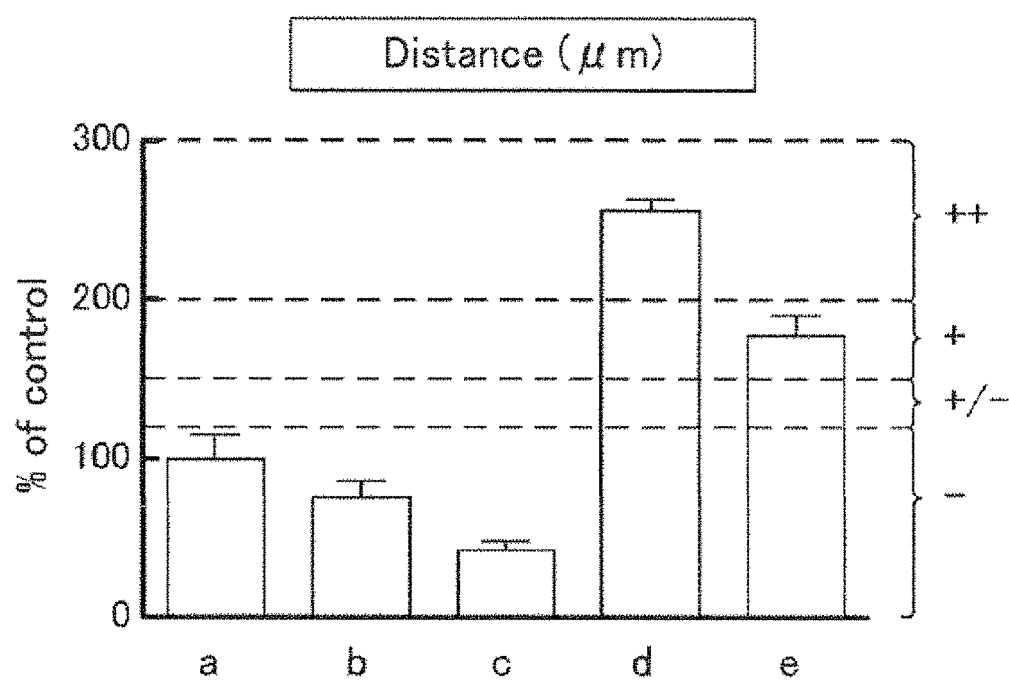
FIG. 3B shows percentages of the migration distance relative to that of the control group (the serum of the healthy volunteer.

For setting criteria for the allergy test, percentages of the migration velocity and the migration distance relative to those of the control group (the serum of the healthy volunteer: a) were calculated (FIGS. 3A and 3B). When the criteria shown in Table 1, which classifies the degrees of the allergy into four classes (strongly positive, ++: positive, suspected, +/−; and negative, −), was used, the results of the test were determined as shown in Table 2. Patient #3 was determined as strongly positive (++) with either of the parameters, the migration velocity and the migration distance, the determination indicating patient #3 developed a strong allergy. Patient #1 and #2 were determined as negative (−) in accordance with the clinical courses. The volunteer with mild cutaneous pruritus was determined as positive or suspected with each parameter. Compared to the actual symptom, the determination seems appropriate. Accordingly, setting and using such criteria is useful for an allergy test.

TABLE 1

| Criterion (% of Control) | <~120 | 120~150 | 150~200 | >200 |
|---|---|---|---|---|
| Judgment | − | +/− | + | ++ |

TABLE 2

| Patient | a | b | c | d | e |
|---|---|---|---|---|---|
| Velocity | − | − | − | ++ | +/− |
| Distance | − | − | − | ++ | + |

Example 2: Detection of Drug Allergy Patient by Utilizing Migration of Cells of Human T-Cell Cell Line (Serum)

Serum was prepared in the substantially same manner as in Example 1.

(Chemotactic Cells)

In place of the leukocytes of the healthy volunteer, an established human T-cell cell line, Jurkat cell (American Type Culture Collection, VA, USA) was used as the chemotactic cells. The cells were suspended in 5 ml of a culture medium (DMEM: Sigma-Aldrich), cultured in a $CO_2$ incubator at 37° C. for 1 hour in the same manner as in Example 1, adjusted to the concentration of about $5\times10^5$ cells/ml, and used as the chemotactic cells. The Jurkat cells were retained in a culture medium for subculture (DMEM containing 10% FBS (JRHBiosciences, KS, USA), 100 U/ml penicillin and 100 µg/ml streptomycin (both Sigma-Aldrich)), with the culture medium exchanged twice a week and, if necessary, the concentration adjusted.

(Measurement of Cell Kinetics)

The cell kinetics was measured in the substantially same manner as in Example 1 excepting that the depth of the terrace was set to 8 µm.

(Analysis of Images)

For determining the cell kinetics, the images were analyzed in the substantially same manner as in Example 1.

(Results)

Figure 4A:
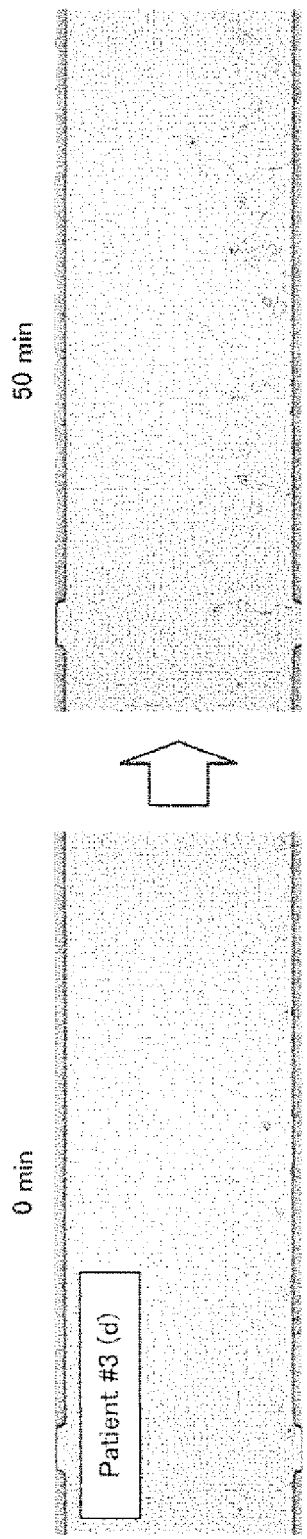
FIG. 4A shows microscopic images of chemotactic test using Jurkat cells in a chemotactic chamber. Serum of #3 patient was added to the upper well of the chamber. The images at the addition of the serum and that at 50 minutes after the addition are shown. The cell kinetics, i.e. migration velocity, was observed and recorded every two minutes for 50 minutes after the addition of the serum.
Figure 4B:
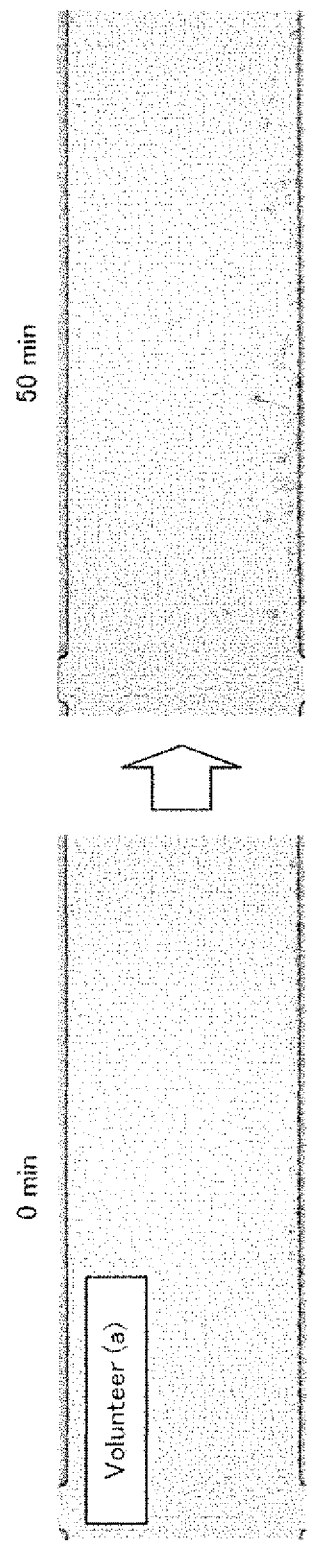
FIG. 4B shows microscopic images of chemotactic test using Jurkat cells in a chemotactic chamber. Serum of a healthy volunteer was added to the upper well of the chamber. The images at the addition of the serum and that 50 minutes after the addition are shown. The cell kinetics, i.e. migration velocity, was observed and recorded every two minutes for 50 minutes after the addition of the serum.
Figure 4C:
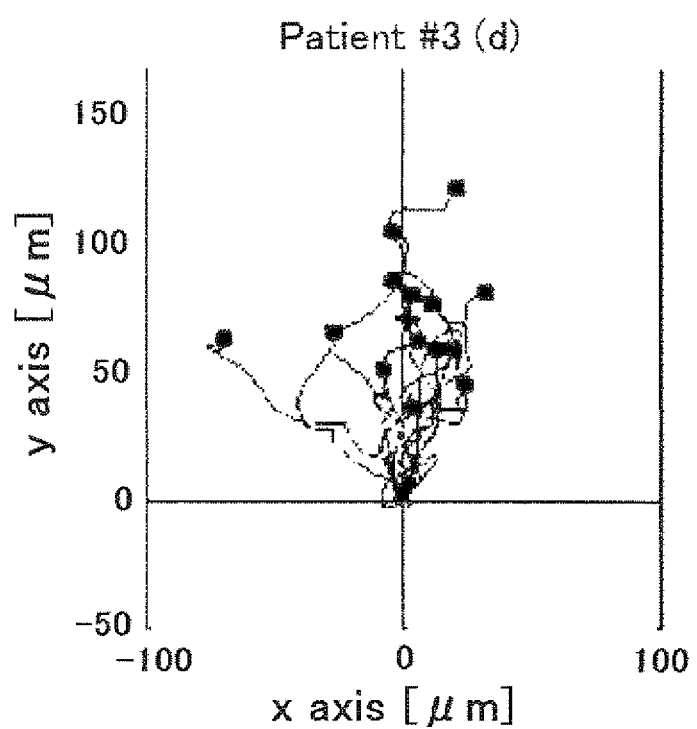
FIG. 4C shows analytical results of the migration distance caused by the serum of patient #3.
Figure 4D:
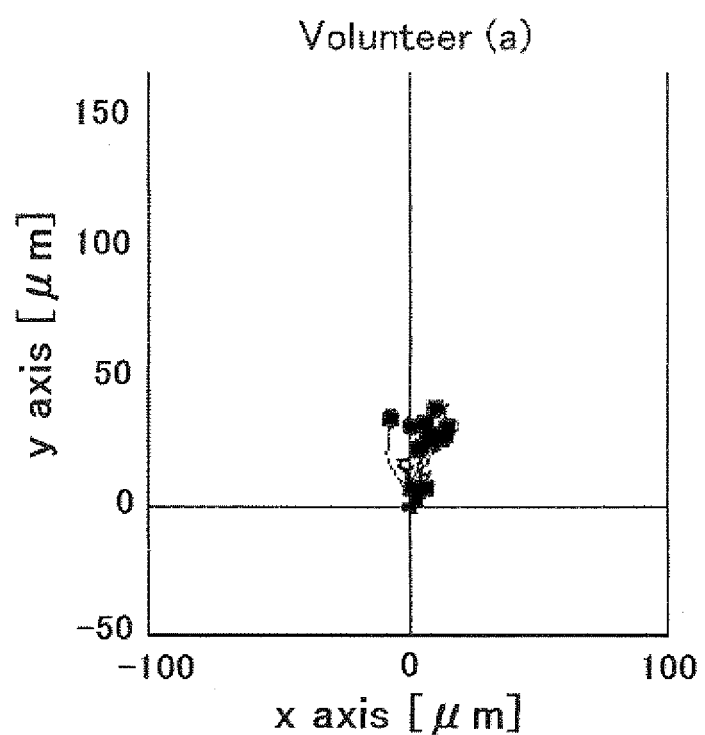
FIG. 4D shows analytical results of the migration distance caused by the serum of the healthy volunteer.

Compared to the cell kinetics of the human leukocytes used in Example 1, the cell kinetics of the Jurkat cells was very slow, the migration velocity was approximately ⅕. Accordingly, images recorded for 50 minutes, rather than 20 minutes, were analyzed (FIGS. 4A and 4B). Similarly to Example 1, the migration velocity of measured for patient #3 (Example 1-d) was significantly larger than that that measured for the healthy volunteer (Example 1-a) as shown in FIGS. 4C to 4E ($p<0.001$). Similar results were obtained for the migration distance though the data is not shown. These results suggest that not only leukocytes containing granulocytes but also an appropriate established cell line may be used for the test, if it is suitable for the purpose of the test (the type of chemotactic factor that is necessary for the test or to be tested).

Example 3: Determination of Allergenic Agent by the Method Provided by the Present Invention (Serum)

Serum was prepared in the substantially same manner as in Example 1 excepting that the subject was patient #3, who was found to clearly have a positive reaction in Example 1.

(Chemotactic Cells)

Chemotactic cells were prepared in the substantially same manner as in Example 1.

(Solution of Antigenic Drug)

A drug solution was prepared by dissolving a drug in a Hank's balanced salt solution (HBSS: Sigma-Aldrich) if the drug was a solid preparation such as a soluble tablet or a powder. If the drug was poorly soluble, it was dissolved in Dimethyl-sulfoxide (DMSO: Sigma-Aldrich) and the solution was diluted with HBSS so that the final concentration of DMSO was 1% or less. A solution containing the drug solution and the serum of the patient in a ratio of 1:1 was used as a solution of the antigenic drug. The concentrations of the suspected drugs were set to ½ of the Cmax in principle. The concentration of phytohemagglutinin (PHA: Wako Pure Chemical Industries, Ltd., Osaka), a control antigen for stimulating or activating the lymphocytes, was set to 1 µg/ml.

(Mononuclear Cells)

Peripheral blood Mononuclear cells (PBMC) were separated from heparinized blood of the patient by density gradient centrifugation (Lymphoprep™: Axis-Shield PoC, Oslo, Norway) in a conventional manner, washed with HBSS, and then adjusted to the concentration of about $5\times10^6$ cells/ml with a culture medium for reaction (RPMI 1640 containing 10% horse serum (Invitrogen, CA, USA)).

(Reactive Solution Stimulated with Antigen)

A mixture of the suspension of the mononuclear cells and the solution of the antigenic drug in a ratio of 4:1 was reacted in a $CO_2$ incubator at 37° C. for 72 hours, and the supernatant was used as a reactive solution stimulated with the antigen. PHA (a), gasmotin (b), dogmatyl (c), pariet (d) and DMSO (e) were used as the antigen.

(Measurement of Cell Kinetics)

The cell kinetics was measured in the substantially same manner as in Example 1 excepting that the reactive solution stimulated with the antigen was injected into the upper well in place of the serum.

(Analysis of Images)

The images were analyzed in the substantially same manner as in Example 1.

(Results)

Figure 5A:
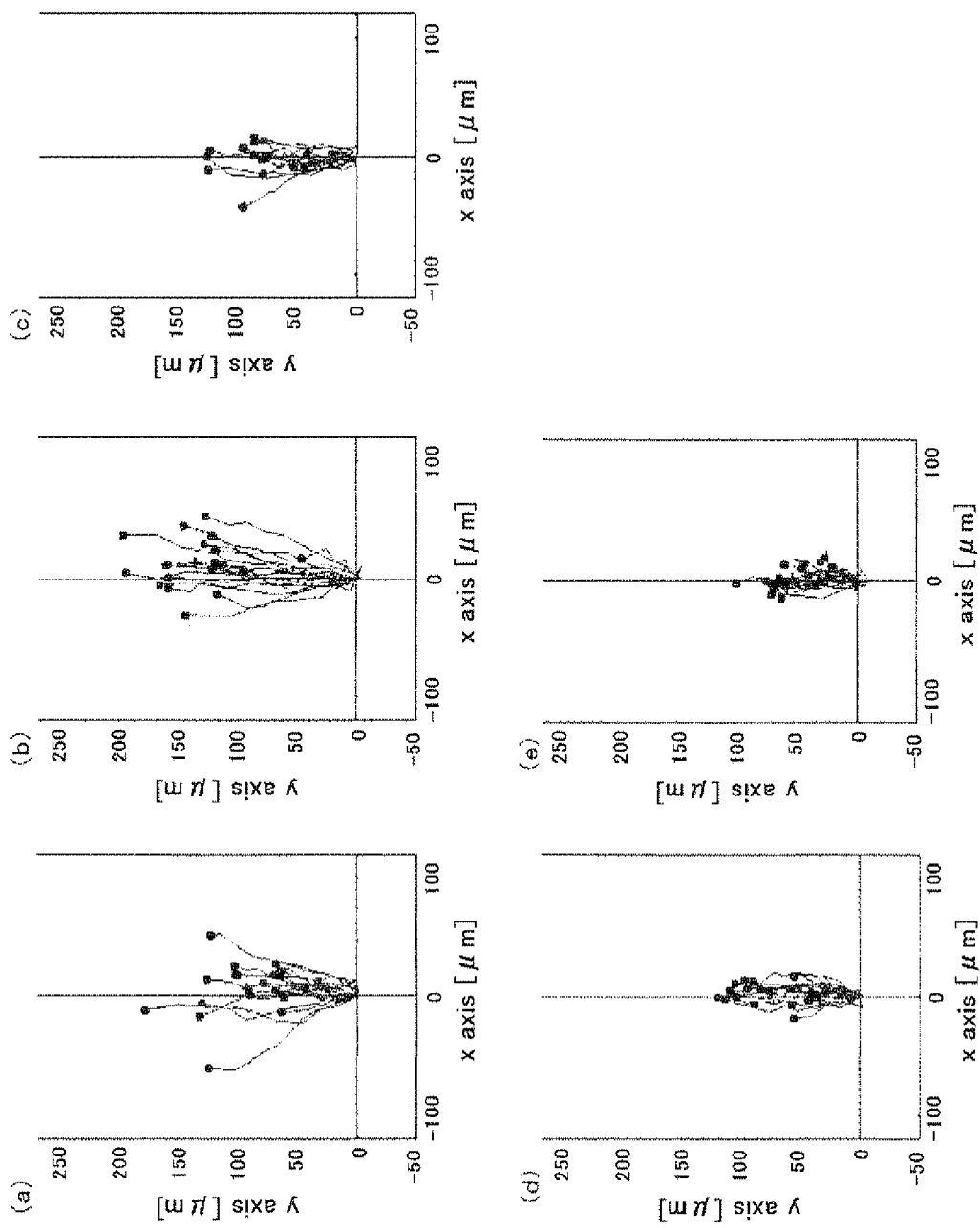
FIG. 5A shows analytical results of chemotaxis or migration ability toward phytohemagglutinin (hereinafter also designated as PHA) (a) as a control, gasmotin (b), other suspected drugs (c and d), and a solvent (DMSO, e).
Figure 5B:
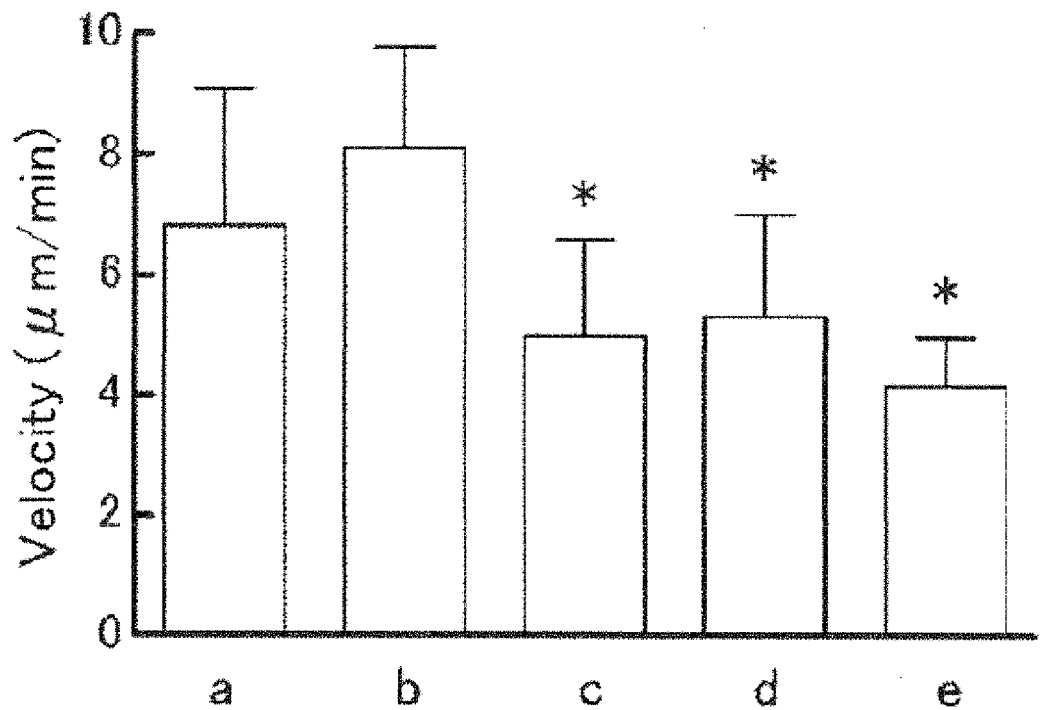
FIG. 5B shows analytical results of the migration velocity.
Figure 5C:
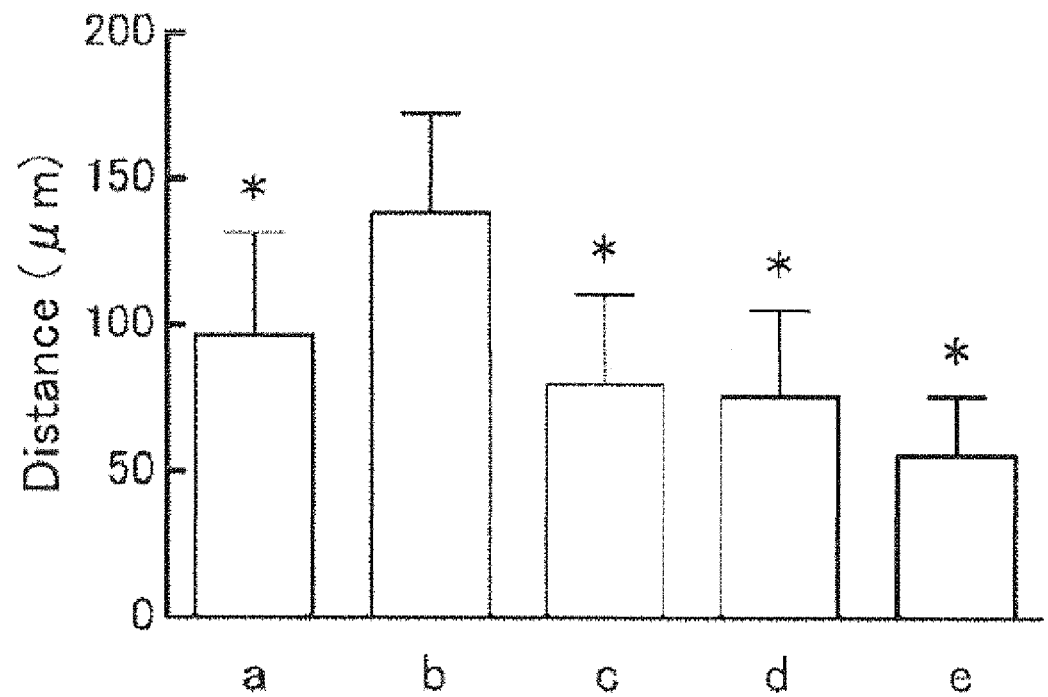
FIG. 5C shows analytical results of the migration distance.

Since human leukocytes were used, images recorded for 20 minutes were used for the analysis as in Example 1. As shown in FIG. 5A, when gasmotin (b) was used as the antigen, rapid migration of the chemotactic cells in the positive direction of the density gradient of the reactive solution stimulated with the antigen, which is similar to that observed with the serum, was observed on the observation terrace. PHA (a) as the control induced the chemotaxis or migration ability weaker than that induced with (b) but stronger than those induced with the other suspected drugs (c and d) or the solvent (DMSO, e). The cell migration of some selected cells was analyzed in detail. The migration velocity (FIG. 5B) and migration distance (FIG. 5C) induced with the suspected drug b was significantly larger than that induced with the other suspected drugs and the solvent (c, d and e). The results strongly suggest that drug b (gasmotin) induced the drug allergy in the patient #3. The symbol "*" in FIGS. 5B and 5C indicates the significant difference from the group of the suspected drug b (p<0.05).

(Criteria)

Figure 6A:
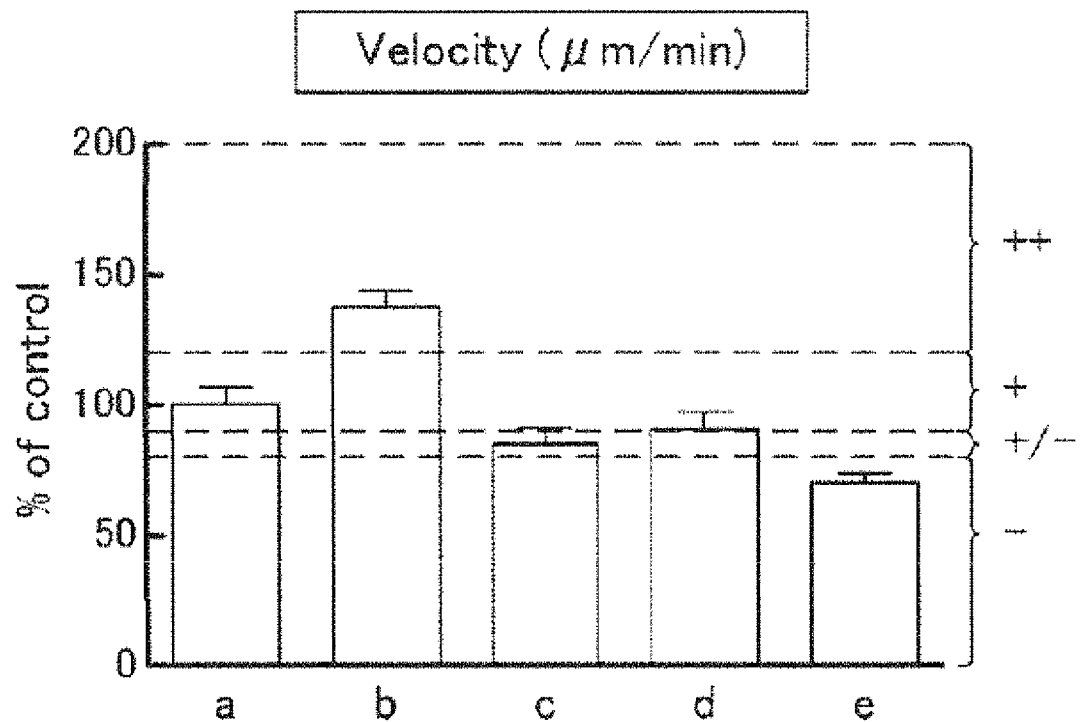
FIG. 6A shows percentages of the migration velocity relative to that of the control group (the reactive solution stimulated with PHA: a).
Figure 6B:
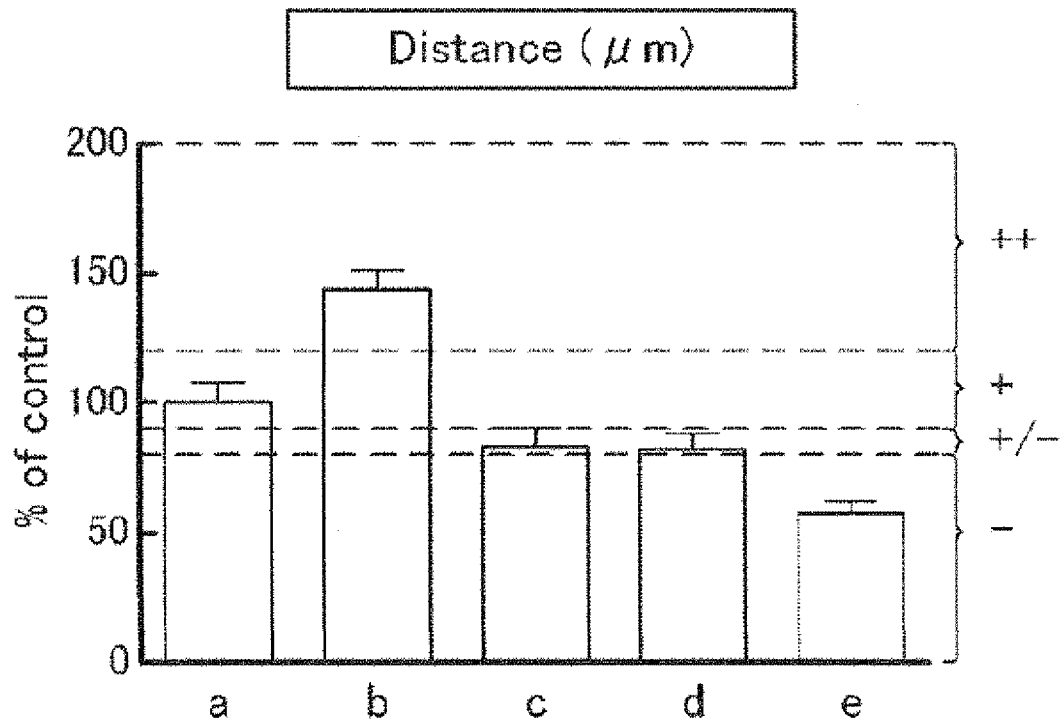
FIG. 6B shows percentages of the migration distance relative to that of the control group (the reactive solution stimulated with PHA: a).

For setting criteria for determining the causative agent that induces the drug allergy or for predicting the allergy in a patient, percentages of the migration velocity and the migration distance relative to that of the control group (the reactive solution stimulated with PHA: a) were calculated (FIGS. 6A and 6B). When the criteria shown in Table 3, which classifies the degrees of the allergy into four classes (strongly positive, ++: positive, +: suspected, +/−; and negative, −), is used, the results of the test are determined as shown in Table 4. Among the suspected drugs for Patient #3, gasmotin (b) was determined as strongly positive (++) with either of the parameters, the migration velocity and the migration distance, the determination indicating that gasmotin (b) was the causative agent inducing the drug allergy. The other suspected drugs and the solvent (c, d and e) were determined as suspected (+/−) or negative (−) particularly on the basis of the migration distance. Since the large change in the chemotaxis of leukocytes was observed in this example by posteriorly stimulating the lymphocytes of the patient having the drug allergy with the drug and the serum, it will be generally possible to determine development of a drug allergy by posteriorly or previously stimulating lymphocytes with the drug. Accordingly, setting and using such criteria is useful for determining a causative agent of an allergy or predicting a drug allergy in a patient.

TABLE 3

| Criterion (% of Control) | <~80 | 80~90 | 90~120 | >120 |
|---|---|---|---|---|
| Judgment | − | +/− | + | ++ |

TABLE 4

| Patient | a | b | c | d | e |
|---|---|---|---|---|---|
| Velocity | + | ++ | +/− | + | − |
| Distance | + | ++ | +/− | +/− | − |

Example 4: Influence of Antigen Concentration on Cell Kinetics of Migrating Cells (Serum)

Serum was prepared in the substantially same manner as in Example 1 excepting that the subject was a volunteer who had a medical history of a cedar pollen allergy but did not develop an allergic symptom at the time of the blood withdrawal (September).

(Chemotactic Cells)

Chemotactic cells were prepared in the substantially same manner as in Example 1.

(Solution of Antigenic Drug)

A cedar pollen antigen SBP (Hayashibara Biochemical Laboratories, Inc., Okayama) was used. The serum was prepared so that the final concentration is 10%.

(Peripheral Blood Mononuclear Cells)

Peripheral blood mononuclear cells (PBMC) were separated from heparinized blood of the volunteer having the medical history of the cedar pollen allergy but not developing the symptom at the time of blood withdrawal by density gradient centrifugation in a conventional manner, washed with PBS, and then adjusted to the concentration of about $5 \times 10^6$ cells/ml with a culture medium for reaction (RPMI 1640 containing 10% FBS).

(Reactive Solution Stimulated with Antigen)

The solutions of the antigenic drug (the cedar pollen antigen SBP: 0, 0.5, 5, or 50 μg/ml) were added to the mononuclear cells, the mixtures were reacted in a $CO_2$ incubator at 37° C. for 72 hours, and the supernatants were used as the reactive solution stimulated with the antigen.

(Measurement of Cell Kinetics)

The cell kinetics was measured in the substantially same manner as in Example 1 excepting that the reactive solutions stimulated with the antigen was injected into the upper well in place of the serum.

(Analysis of Images)

The images were analyzed in the substantially same manner as in Example 1.

(Results)

Figure 7A:
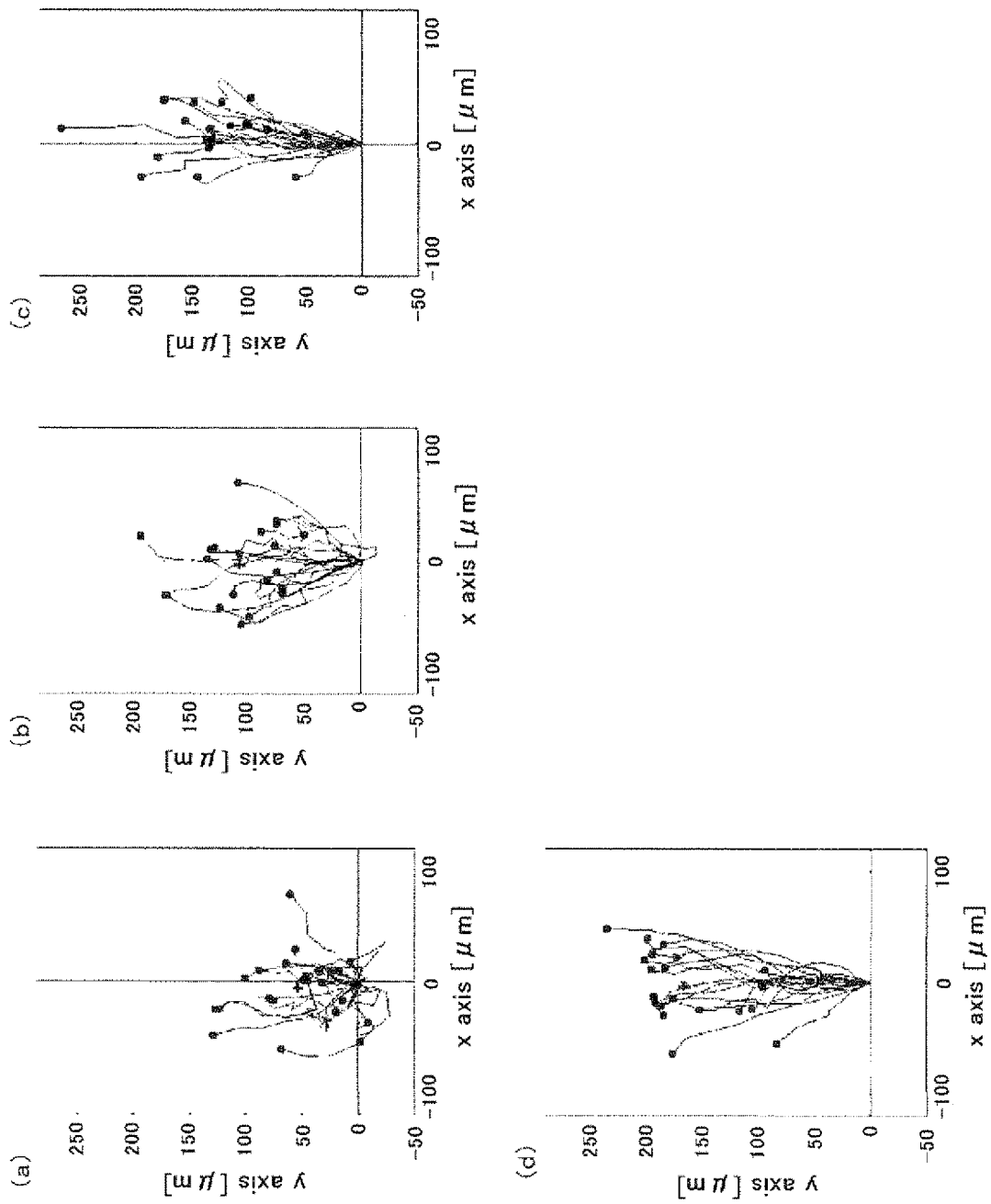
FIG. 7A shows analytical results of chemotaxis or migration ability toward a cedar pollen antigen SBP.
Figure 7B:
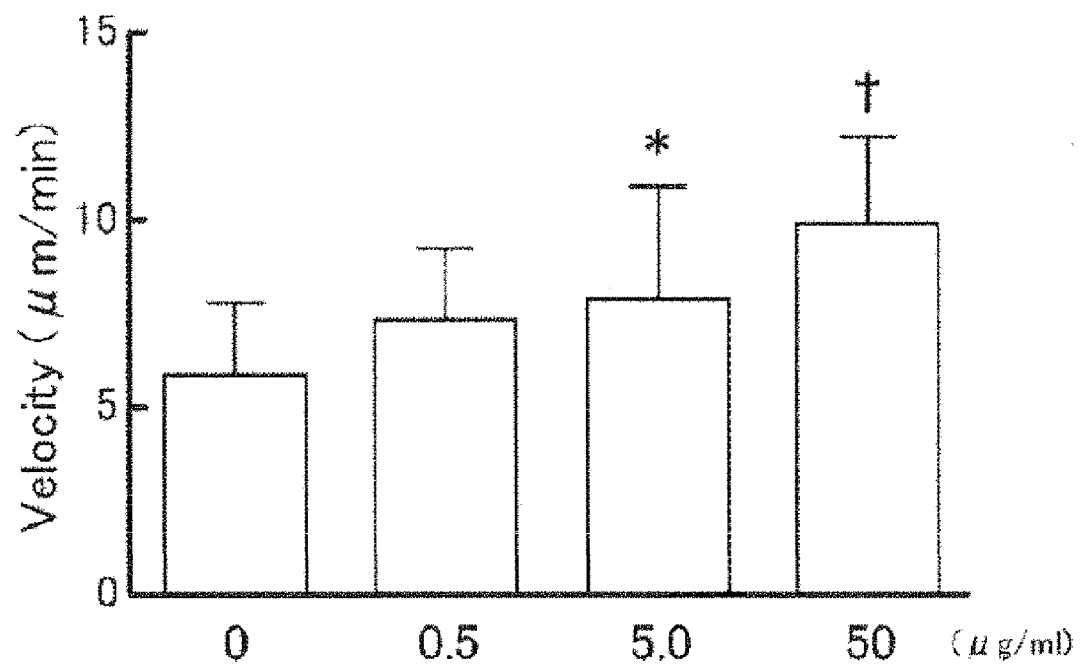
FIG. 7B shows analytical results of the migration velocity.
Figure 7C:
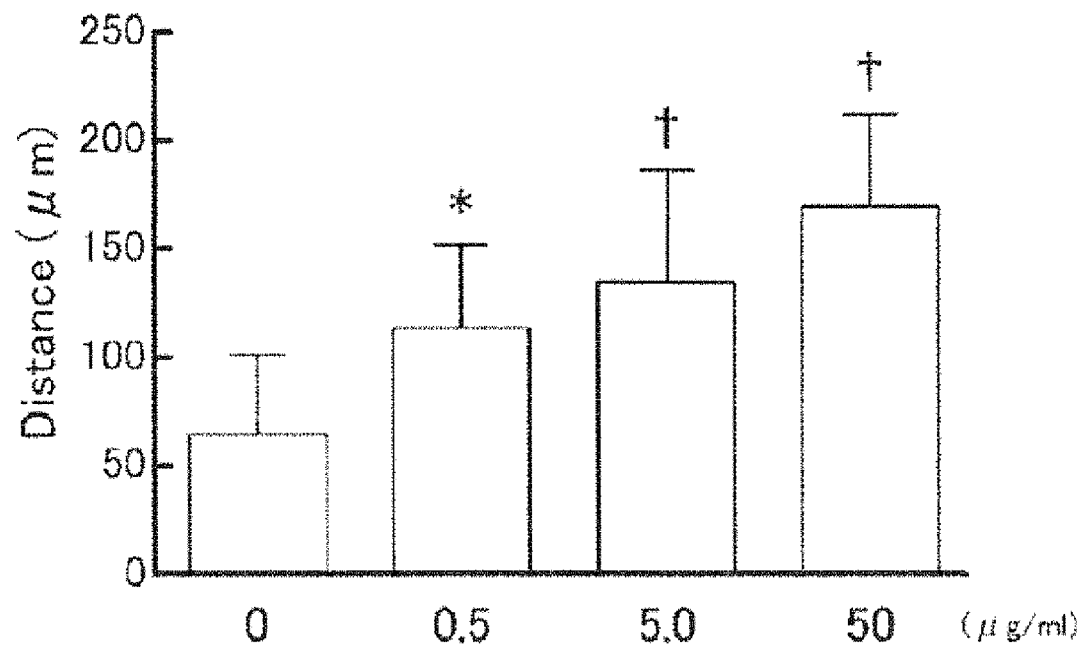
FIG. 7C shows analytical results of the migration distance.

In the same manner as in Example 3, the activation and migration of the chemotactic cells in the positive direction of the density gradient of the reactive solution stimulated with the antigen, the cedar pollen antigen SBP, was observed on the observation terrace (FIG. 7A). The cells were activated depending on the concentration of the antigen. The cell migration of some selected cells was analyzed in detail. As expected, the migration velocity (FIG. 7B) and the migration distance (FIG. 7C) significantly increased depending on the concentration of the antigen (*: p<0.01, †: p<0.001).

(Criteria)

Figure 8A:
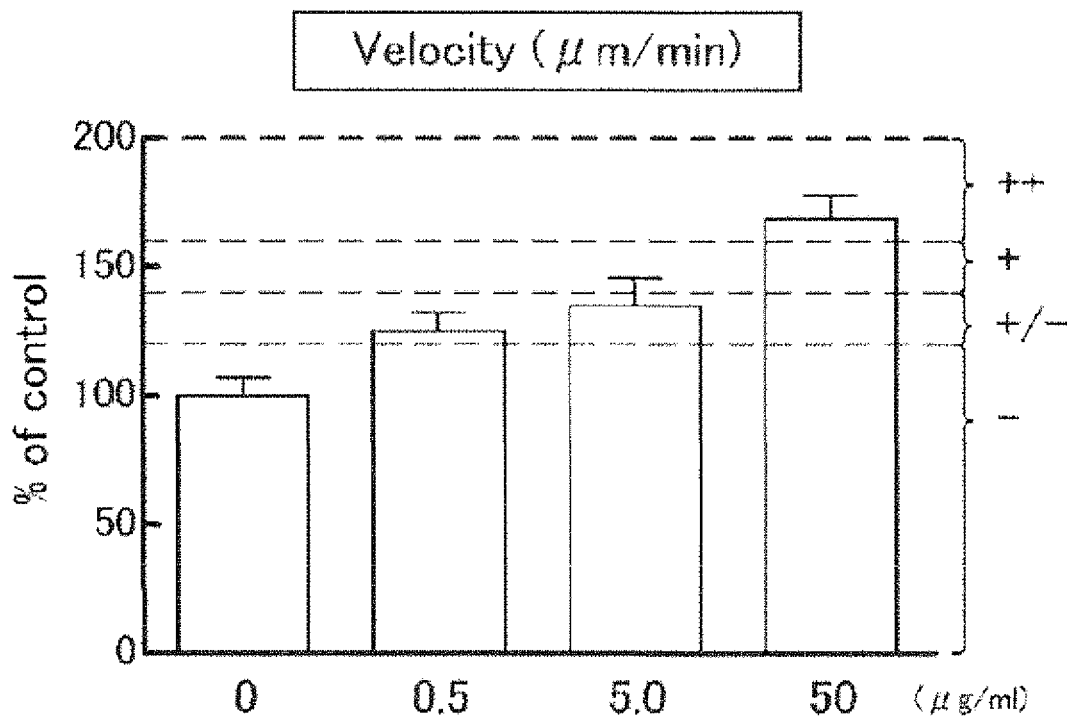
FIG. 8A shows percentages of the migration velocity relative to that of the control group (the cedar pollen antigen SBP: 0 μg/ml).
Figure 8B:
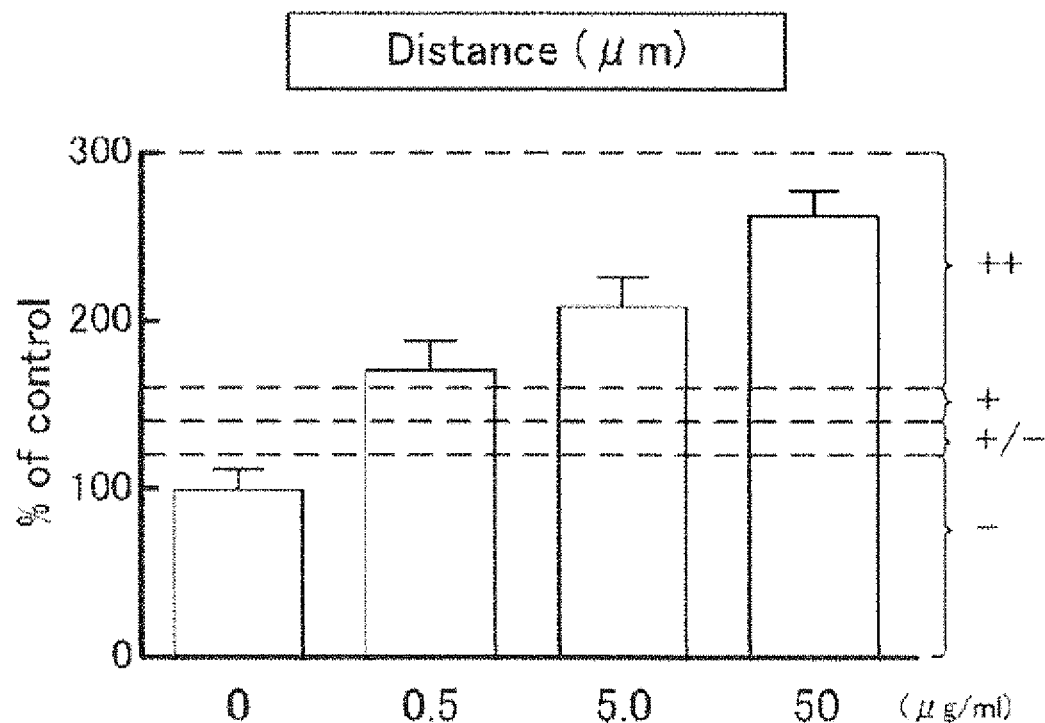
FIG. 8B shows percentages of the migration distance relative to that of the control group (the cedar pollen antigen SBP: 0 μg/ml).

For setting criteria for predicting development of the allergy, percentages of the migration velocity and the migration distance relative to that of the control group (the cedar pollen antigen SBP=0 μg/ml) were calculated (FIGS. 8A and 8E). When the criteria shown in Table 5, which classifies the degrees of the allergy into four classes (strongly positive, ++: positive, +: suspected, +/−; and negative, −), is used, the results of the test are determined as shown in Table 6. The subject was determined as strongly positive (++) or suspected (+/−) with either of the parameters, the determination indicating that the pollen allergy was induced. The determination can predict that the subject is very likely to develop a serious pollen allergy when the subject is exposed to cedar pollen in future. Accordingly, it is suggested that a novel method for predicting development of an allergy in the absence of an allergic symptom can be provided, the method using a reactive solution stimulated with an antigen which is prepared by stimulating lymphocytes and serum of a subject with an antigen, determining and analyzing chemotaxis or migration ability of chemotactic cells, and applying an appropriate criteria to the result.

TABLE 5

| Criterion (% of Control) | <~120 | 120~140 | 140~160 | >160 |
|---|---|---|---|---|
| Judgment | − | +/− | + | ++ |

TABLE 6

| Conc. (μg/ml) | 0 | 0.5 | 5.0 | 50 |
|---|---|---|---|---|
| Velocity | − | +/− | +/− | ++ |
| Distance | − | ++ | ++ | ++ |

Figure 9:
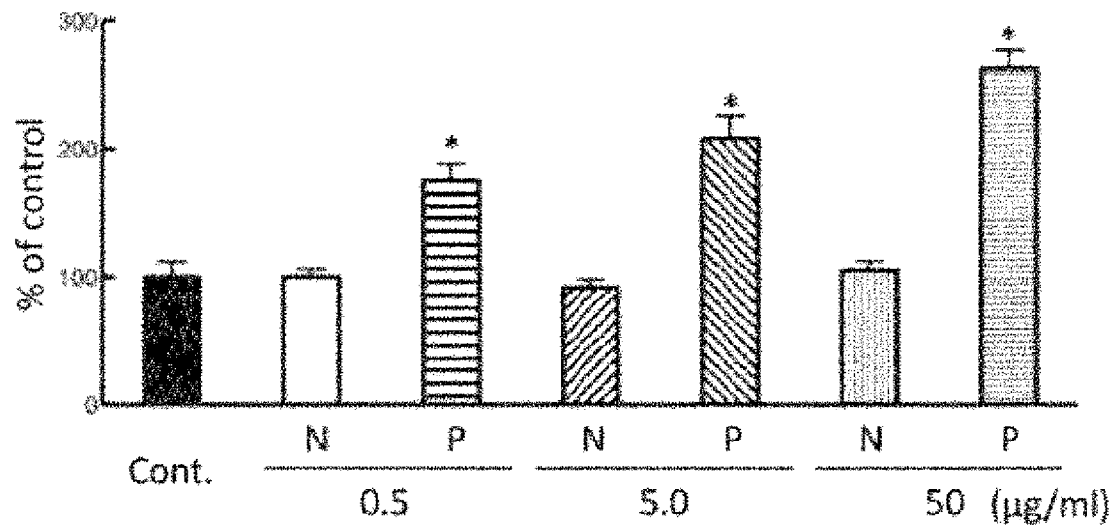
FIG. 9 shows increase of the cell kinetics depending on the pollen extract concentration.

Example 5: Influence of Stimulation with Pollen Extract to Cell Kinetics in the Presence or Absence of Pollen Allergy in Subject (Chemotactic Cells)
Chemotactic cells were prepared in the substantially same manner as in Example 1.
(Solution of Antigenic Drug)
A cedar pollen antigen SBP (Hayashibara Biochemical Laboratories, Inc., Okayama) was used. The serum was prepared so that the final concentration is 10%.
(Peripheral Blood Mononuclear Cells)
Peripheral blood mononuclear cells (PBMC) were separated from heparinized blood of a patient having a cedar pollen allergy and a healthy volunteer having no pollen allergy by density gradient centrifugation in a conventional manner, washed with PBS, and then adjusted to the concentration of about $5\times10^6$ cells/ml with a culture medium for reaction (RPMI 1640 containing 10% FBS).
(Reactive Solution Stimulated with Antigen)
The solutions of the antigenic drug (the cedar pollen antigen SBP: 0, 0.5, 5, or 50 μg/ml) were added to the mononuclear cells, the mixtures were reacted in a $CO_2$ incubator at 37° C. for 72 hours, and the supernatants were used as the reactive solution stimulated with the antigen.
(Measurement of Cell Kinetics)
The cell kinetics was measured in the substantially same manner as in Example 1 excepting that the reactive solutions stimulated with the antigen were injected into the upper well in place of the serum.
(Image Analysis)
The images were analyzed in the substantially same manner as in Example 1.
In the test using the mononuclear cells exposed to the pollen extract, cell kinetics of the leukocytes of a healthy volunteer was clearly different between the subject having the pollen allergy and the subject having no pollen allergy. When the subject had no pollen allergy, the cell kinetics of the leukocytes of the healthy volunteer was not affected at all by the supernatant of the mononuclear cells stimulated with the pollen extract. On the other hand, when the subject had a pollen allergy, the motility of the leukocytes of the healthy volunteer caused by the supernatant of the stimulated mononuclear cells increased depending on the concentration of the pollen extract (FIG. 9) (*: p<0.01). This result indicates that mononuclear cells of a patient of a pollen allergy secretes upon stimulation with pollen a chemotactic factor which is different from those of a healthy human, and that the chemotactic factor causes migration of leukocytes of a healthy human.

Figure 10A:
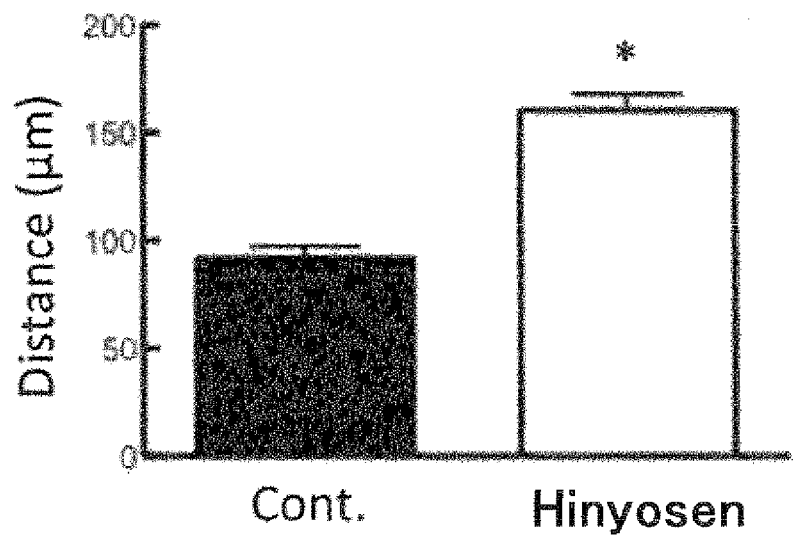
FIG. 10A shows influence of Hinyosen on the cell kinetics.
Figure 10B:
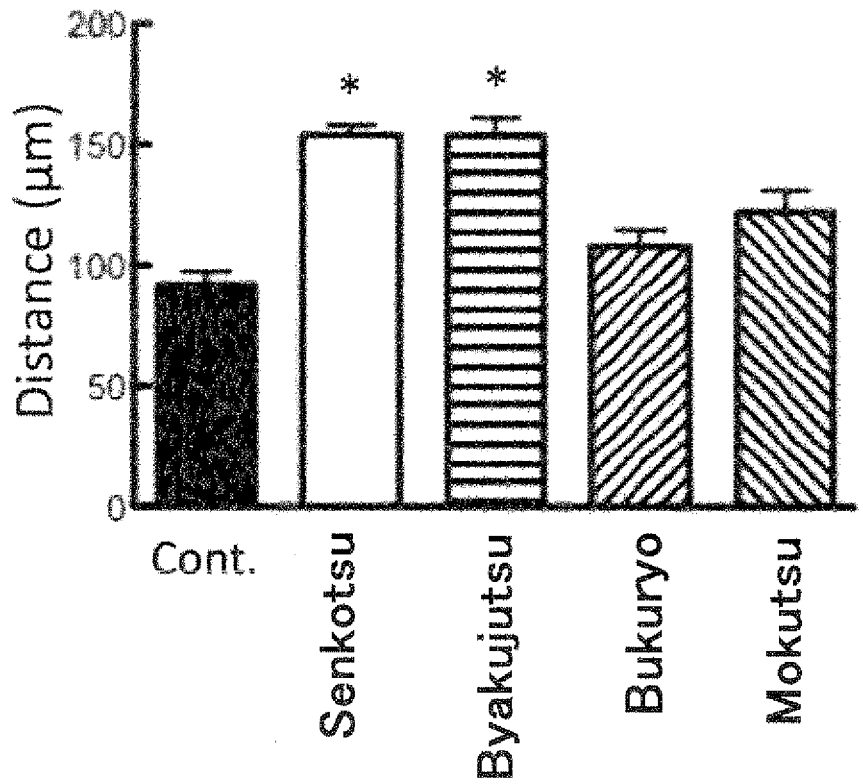
FIG. 10B shows influence of each component of the Kampo product on the cell kinetics.

Example 6: Diagnosis of Subject Having Allergy to Kampo Product and Determination of Allergenic Agent by Method Provided by the Present Invention (Chemotactic Cells)
Chemotactic cells were prepared in the substantially same manner as in Example 1.
(Solution of Antigenic Drug)
To 550 ml of purified water, 18 g of a Kampo product (Nagakura Hinyosen) was added, and the mixture was heated and concentrated to the volume of 330 ml, filtered through a paper filter to give a decoction of the Kampo product. Decoctions of four components of the Kampo product, Senkotsu (*Nuphar japonicum*), Byakujutsu (*Atractylodes japonica*), Bukuryo (*Wolfiporia extensa*) and Mokutsu (*Akebia quinata*), were also prepared.
(Peripheral Blood Mononuclear Cells)
Peripheral blood mononuclear cells (PBMC) were separated from heparinized blood of a patient having a cedar pollen allergy and a healthy volunteer having no pollen allergy by density gradient centrifugation in a conventional manner, washed with PBS, and then adjusted to the concentration of about $5\times10^6$ cells/ml with a culture medium for reaction (RPMI 1640 containing 10% FBS).
(Reactive Solution Stimulated with Antigen)
A mixture of the mononuclear cells and the solution of the antigenic drug was reacted in a $CO_2$ incubator at 37° C. for 72 hours, and the supernatant was used as a reactive solution stimulated with the antigen.
(Measurement of Cell Kinetics)
The cell kinetics was measured in the substantially same manner as in Example 1 excepting that the reactive solution stimulated with the antigen was injected into the upper well in place of the serum.
(Analysis of Images)
The images were analyzed in the substantially same manner as in Example 1.
The mononuclear cells of a patient, who had an allergy-like symptom after taking the Kampo product (Nagakura Hinyosen), were exposed to the suspected drug, the decoction of the Kampo product (1:10,000), and the influence of the culture supernatant on the cell kinetics of the leukocytes of a healthy volunteer was examined. The exposure of the mononuclear cells of the patient to the Kampo product induced production and release of a chemotactic factor from the cells, and the chemotactic factor affected the cell kinetics of the leukocytes of the healthy volunteer. The result suggests that the subject has developed an allergy (FIG. 10A) (*: p<0.01).
Decoctions of each component of the Kampo product (senkotsu, byakujutsu, bukuryo and mokutsu) were prepared and tested. Senkotsu and byakujutsu induced very strong reactions similar to that of the Hinyosen. The subject is thought to have a strong allergic reaction to these two components of the Kampo product. The result suggests that the subject should avoid taking a product such as a medicine containing these components (FIG. 10B) (*: p<0.01).

Example 7: Comparison Between Diagnosis by Method Provided by the Present Invention and Diagnosis by DLST or LMT (Serum)
Blood samples from a patient who developed a typical allergy-like symptom and a patient with no such symptom were added with a serum separating agent and allowed to stand at room temperature. Serum was separated by centrifugation at 2,000 rpm for 30 minutes or by using Tube 21 (Registered Trademark)—S(Sekisui Chemical Co., Ltd., Osaka).

(Chemotactic Cells)
Chemotactic cells were prepared in the substantially same manner as in Example 1.

(Solution of Antigenic Drug)
A drug solution was prepared by dissolving a drug in a Hank's balanced salt solution (HBSS: Sigma-Aldrich) if the drug was a solid preparation such as a soluble tablet or a powder. If the drug was poorly soluble, it was dissolved in Dimethyl-sulfoxide (DMSO: Sigma-Aldrich) and the solution was diluted with HBSS so that the final concentration of DMSO was 1% or less. A solution containing the drug solution and the serum of the patient in a ratio of 1:1 was used as a solution of the antigenic drug. The concentrations of the suspected drugs were set to ½ of the Cmax in principle. The concentration of phytohemagglutinin (PHA: Wako Pure Chemical Industries, Ltd., Osaka), a control antigen for stimulating or activating lymphocytes, was set to 1 μg/ml.

(Antigen Stimulation Reaction Solution)
A mixture of the mononuclear cells and the solution of the antigenic drug was reacted in a $CO_2$ incubator at 37° C. for 72 hours, and the supernatant was used as a reactive solution stimulated with an antigen.

(Peripheral Blood Mononuclear Cells)
Peripheral blood mononuclear cells (PBMC) were separated from heparinized blood of the patient who developed the typical allergy-like symptom and the patient with no such symptom by density gradient centrifugation in a conventional manner, washed with PBS, and then adjusted to the concentration of about $5 \times 10^6$ cells/ml with a culture medium for reaction (RPMI 1640 containing 10% FBS).

(Measurement of Cell Kinetics)
The cell kinetics was measured in the substantially same manner as in Example 1.

(Analysis of Images)
The images were analyzed in the substantially same manner as in Example 1.

The patient having the typical allergy-like symptom (skin lesion) and the atypical patient were tested by the three different methods, namely the DLST, which is widely used for clinical tests, the LMT, which is sometimes reported more accurate than the DLST, and the present method, and then the results were compared. As shown in Table 7, the atypical case (patient A) and the typical case (patient B) were determined as negative by the DLST and the LMT, which are currently employed as the primary testing methods. The typical case was determined as negative though the patient clearly developed the skin symptom of the toxic epidermal necrolysis (TEN) according to the clinical presentation and the clinical course.

Figure 11:
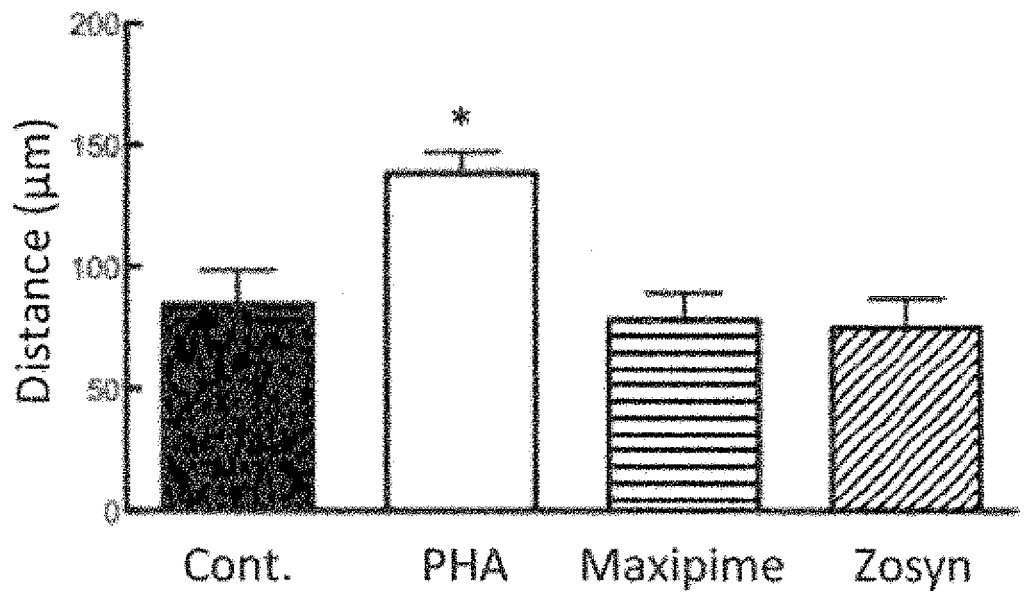
FIG. 11 shows atypical negative test results of the method provided by the present invention. The patient did not have any serious and typical allergy-like skin symptom.

On the other hand, the method provided by the present invention determined that the cell kinetics of the atypical case was negative for all the suspected drugs excluding PHA, the positive control, providing the same result as those of the DLST and the LMT (FIG. 11) (*: p<0.01). These results suggest that the symptom of the atypical patient was caused by a cause other than the allergy.

Figure 12:
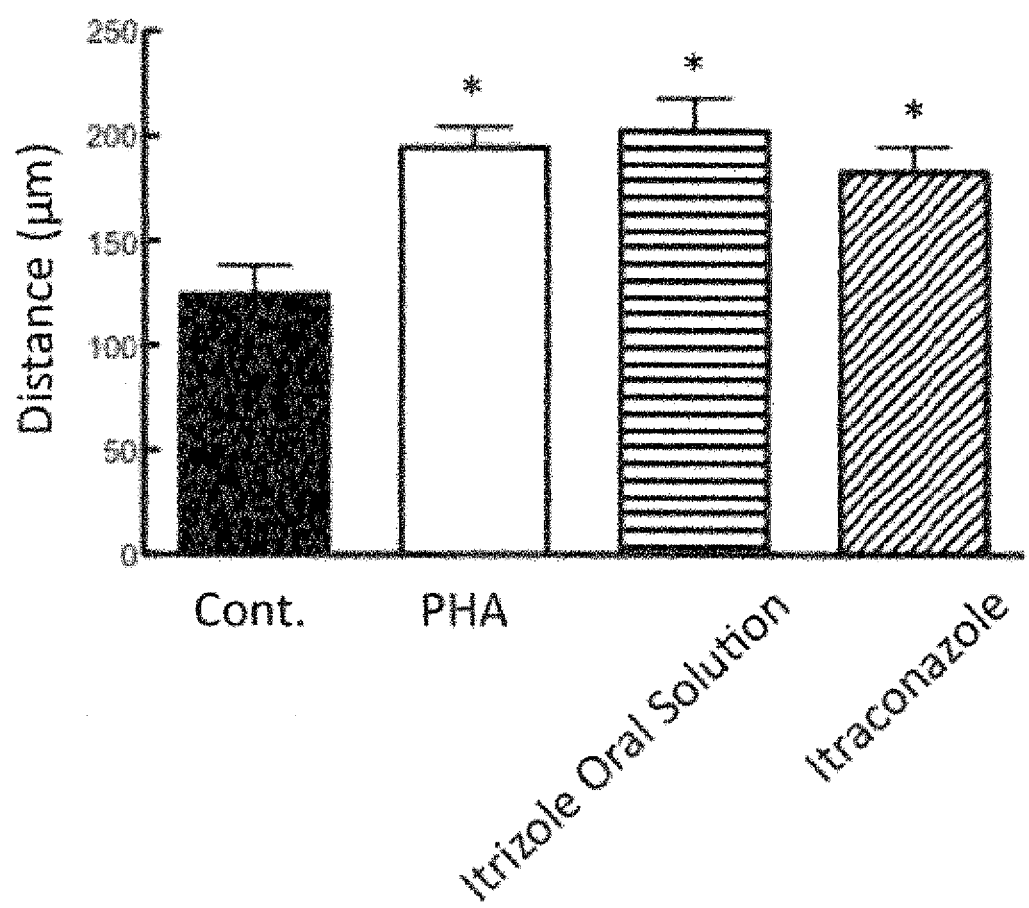
FIG. 12 shows typical positive test results of the method provided by the present invention. The patient had serious and typical allergy-like skin symptoms.

The method provided by the present invention, unlike the DLST and the LMT, determined that the two suspected drugs as well as the oral preparations containing the drugs were positive in the typical case (FIG. 12) (*: p<0.01), Accordingly, the method provided by the present invention revealed that the suspected drug (the medical ingredient) caused the development of the TEN.

TABLE 7

| Patient/ Suspected drug | Patient A | | | Patient B | | | | |
| --- | --- | --- | --- | --- | --- | --- | --- | --- |
| | PHA | Maxipime | Zosyn | PHA | Itrizole test 1 | Itrizole test 2 | Itraconazole test 1 | Itraconazole test 2 |
| DLST (SI value)* | + | 112 | 124 | + | 100 | 100 | 151 | 90 |
| LMT (MI value)# | 154.87 | 88.21 | 98.42 | 283.9 | ND | 110.7 | ND | 135.5 |

Positive with *SI value > 180 (DLST), #MI value > 150 and p < 0.05 (LMT); ND, not determined.

Example 8: Detection of Allergenic Agent Using Human Promyelocytic Cell Line: HL-60 Cells (Serum)
Serum of a healthy human was prepared in the same manner as in Example 1.

(Chemotactic Cells)
A human promyleocytic cell line: HL-60 cells were used as chemotactic cells. The cells were suspended in 5 ml of a culture medium (RPMI 1640), cultured in a $CO_2$ incubator at 37° C. for 1 hour, adjusted to the concentration of about $5 \times 10^5$ cells/ml, and used as the chemotactic cells. The HL-60 cells were retained in a culture medium for subculture (DMEM containing 10% FBS (JRHBiosciences, KS, USA), 100 U/ml penicillin and 100 μg/ml streptomycin (bath Sigma-Aldrich)), with the culture medium exchanged and, if necessary, the concentration adjusted twice a week.

(Solution of Antigenic Drug)
A cedar pollen antigen SBP (Hayashibara Biochemical Laboratories, Inc., Okayama) was used. The concentration was adjusted to be at 50 μg/ml after the addition of the antigen to the mononuclear cells.

(Peripheral Blood Mononuclear Cell)
Peripheral blood mononuclear cells (PBMC) were separated from heparinized blood of a patient having a cedar pollen allergy by density gradient centrifugation in a conventional manner, washed with PBS, and then adjusted to the concentration of about $5 \times 10^6$ cells/ml with a culture medium for reaction (RPMI 1640 containing 10% FBS).

(Reactive Solution Stimulated with Antigen)
Serum of a healthy human or a pollen extract diluted with serum of the healthy human was added to the mononuclear cells, the mixtures were reacted in a $CO_2$ incubator at 37° C. for 72 hours, and the supernatants were used as the reactive solution stimulated with the antigen.

(Measurement of Cell Kinetics)

The cell kinetics was measured in the same manner as in Example 4.

(Analysis of Images)

The images were analyzed in the same manner as in Example 4.

Figure 13:
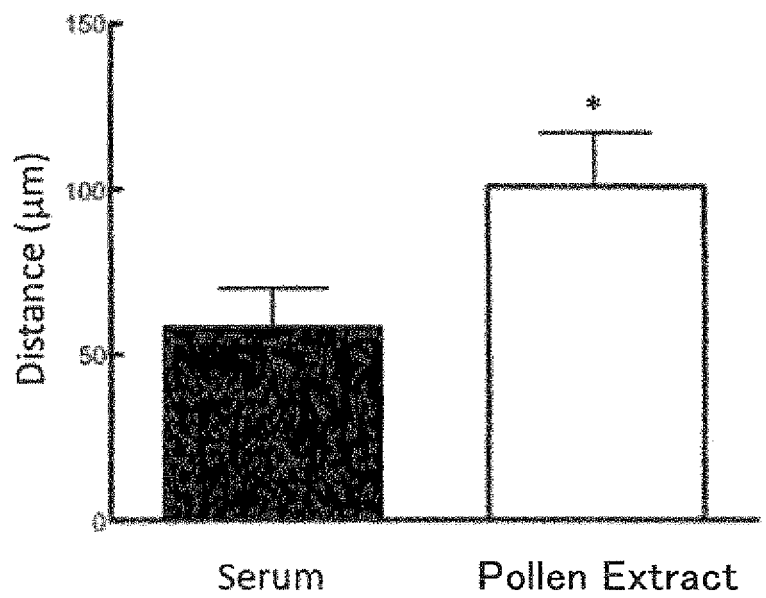
FIG. 13 shows increase of migration distance of HL-60 cells caused by the culture supernatant of mononuclear cells obtained from a patient having cedar pollen allergy and exposed to a pollen extract.

The culture supernatant of the mononuclear cells of the patient having a cedar pollen allergy that was exposed to the pollen extract increased the migration distance of the HL-60 cells (FIG. 13). The result indicates that the mononuclear cells of the patient having a cedar pollen allergy secreted a chemotactic factor which is not present in the serum of the healthy human after the exposure to the pollen extract, and that the chemotactic factor affects the cell kinetics of the HL-60 cells.

The invention claimed is:

1. A method for testing whether or not a sample is allergenic to a subject before the subject develops an allergy to the sample, comprising the steps of:
   (1) obtaining leukocyte cells from the subject;
   (2) culturing the leukocyte cells in a medium containing the sample;
   (3) collecting the culture supernatant;
   (4) creating a concentration gradient of the culture supernatant;
   (5) placing chemotactic cells in the concentration gradient of the culture supernatant; and
   (6) measuring the migration distance and/or migration velocity of the chemotactic cells,
   wherein the chemotactic cells are leukocyte cells derived from a healthy animal or cells of leukocytic cell line, and
   wherein steps (2) to (6) are also carried out by using phytohemagglutinin as a positive control in place of the sample, and
   (i) the sample is determined to be allergenic to the subject when the migration distance of the chemotactic cells placed in the concentration gradient of the culture supernatant prepared with the sample is equivalent to or longer than that of the chemotactic cells placed in the concentration gradient of the culture supernatant prepared with the phytohemagglutinin; and/or
   (ii) the sample is determined to be allergenic to the subject when the migration velocity of the chemotactic cells placed in the concentration gradient of the culture supernatant prepared with the sample is equivalent to or higher than that of the chemotactic cells placed in the concentration gradient of the culture supernatant prepared with the phytohemagglutinin.

2. The method according to claim 1, wherein the allergy is a pollen allergy, a chemical allergy, a drug allergy or a food allergy.

3. The method according to claim 1, wherein the chemotactic cells are cells of a T-cell cell line or a promyelocytic cell line.

4. The method according to claim 3, wherein the chemotactic cells are Jurkat cells or HL-60 cells.

5. The method according to claim 1, wherein cell kinetics of the cells are sequentially recorded over time, and the migration distance or the migration velocity of the cells is determined on the basis of the record over time.

6. The method according to claim 1, wherein the subject is a human.

7. The method according to claim 6, wherein the chemotactic cells are leukocyte cells derived from a healthy human.

8. The method according to claim 6, wherein the chemotactic cells are cells of a leukocytic cell line.

9. The method according to claim 1, wherein steps (2) to (6) are also carried out by using leukocyte cells derived from a healthy animal not having an allergy to the sample as a negative control in place of the leukocytes derived from the subject.

* * * * *